United States Patent [19]

Neises et al.

[11] Patent Number: 5,391,705
[45] Date of Patent: Feb. 21, 1995

[54] POLYFLUORINATED TRIPEPTIDE THROMBIN INHIBITORS

[75] Inventors: Bernhard Neises, Offenburg-Griesheim, Germany; Axel Ganzhorn, Lingolsheim; Céline Tarnus, Strasbourg, both of France; Robert J. Broersma, Jr., Noblesville, Ind.

[73] Assignee: Merrell Dow Pharmaceuticals Inc., Cincinnati, Ohio

[21] Appl. No.: 199,039

[22] Filed: Feb. 18, 1994

Related U.S. Application Data

[63] Continuation of Ser. No. 8,253, Jan. 25, 1993, abandoned, which is a continuation of Ser. No. 848,444, Mar. 9, 1992, abandoned.

[30] Foreign Application Priority Data

Mar. 15, 1991 [EP] European Pat. Off. ........... 91400713

[51] Int. Cl.$^6$ ..................... A61K 37/02; A61K 37/64; C07K 5/08
[52] U.S. Cl. .................................. 530/331; 546/146; 546/145; 546/155; 548/468; 548/532; 548/538
[58] Field of Search ............ 530/331; 514/18, 20, 514/343, 422, 423; 546/145, 146, 153; 548/468, 532, 538

[56] References Cited

U.S. PATENT DOCUMENTS

| | | | |
|---|---|---|---|
| 4,061,625 | 12/1977 | Ekenstam et al. | 530/331 |
| 4,216,142 | 8/1980 | Ali | 530/331 |
| 4,217,269 | 8/1980 | Cole | 548/538 X |
| 4,221,706 | 9/1980 | Ali et al. | 530/332 |
| 4,247,454 | 1/1981 | Ekenstam et al. | 530/331 |
| 4,275,153 | 6/1981 | Gargiulo et al. | 530/331 X |
| 4,318,904 | 3/1982 | Shaw et al. | 530/331 X |
| 4,450,105 | 5/1984 | Nagasawa et al. | 548/538 |
| 4,643,991 | 2/1987 | Digenis et al. | 530/331 X |
| 4,720,484 | 1/1988 | Vincent et al. | 514/18 |
| 4,762,821 | 8/1988 | Nestor | 530/331 X |
| 4,816,560 | 3/1989 | Verdini et al. | 530/331 X |
| 4,816,562 | 3/1989 | Nagasawa et al. | 530/331 X |
| 4,826,814 | 5/1989 | Sawayama et al. | 514/18 |
| 4,880,780 | 11/1989 | Trainor et al. | 514/18 |
| 4,929,602 | 5/1990 | Harker et al. | 514/18 |
| 5,053,392 | 10/1991 | Klein et al. | 514/18 |

FOREIGN PATENT DOCUMENTS

| | | | |
|---|---|---|---|
| 0195212 | 4/1986 | European Pat. Off. | 548/538 |
| 0185390 | 6/1986 | European Pat. Off. | 514/18 |
| 0192135 | 8/1986 | European Pat. Off. | 530/331 |
| 0410411 | 1/1991 | European Pat. Off. | 514/18 |
| 0498508 | 2/1992 | European Pat. Off. | 514/18 |

OTHER PUBLICATIONS

Chem Absts, vol. 110, p. 709, 1989, No. 76058; Angliker et al III "Synthesis and properties of peptidyl derivatives of arginylfluoromethames" (Biochemical Journal, vol. 256, No. 2, pp. 481–486.

Angliker et al. I, Biochem.J. 256(2), 481–6 (1988).

Gelb et al., "Fluoro Ketone Inhibitors of Hydrolytic Enzymes," Biochemistry, vol. 24, No. 8, pp. 1813–1817, 1985.

Sham et al., "Highly potent and specific inhibitors of human renin", FEBS Letters, vol. 220, No. 2, pp. 299–301, 1987.

Chem Absts, vol. 107, 1987, No. 40336Y, p. 758; Stueber, M: "Oligopeptidylargininol derivatives and their homologs, their use as antithrombics and agents containing them".

Shuman et al., Proceedings of the 12th American Peptide Symposium, pp. 801–802, (1991).

*Primary Examiner*—Floyd D. Higel
*Attorney, Agent, or Firm*—William R. Boudreaux

[57] ABSTRACT

This invention relates to novel polyfluorinated alkyl derivatives of certain tripeptides, to the methods for their preparation, the intermediates therefore, to their use in inhibiting thrombin and lung tryptase and in their end-use application as anti-coagulants useful in treating thrombophlebitis and coronary thrombosis and in the treatment of asthma.

12 Claims, No Drawings

POLYFLUORINATED TRIPEPTIDE THROMBIN INHIBITORS

CROSS-REFERENCE TO RELATED APPLICATION

This is a continuation of application Ser. No. 08/008,253, filed Jan. 25, 1993, which is a continuation of application Ser. No. 07/848,444, filed Mar. 9, 1992, both now abandoned.

This invention relates to novel polyfluorinated alkyl derivatives of certain tripeptides, to the methods for their preparation, the intermediates therefore, to their use in inhibiting thrombin and lung tryptase and in their end-use application as anti-coagulants useful in treating thrombophlebitis and coronary thrombosis and in the treatment of asthma. More specifically this invention relates to the novel compounds of the formulae

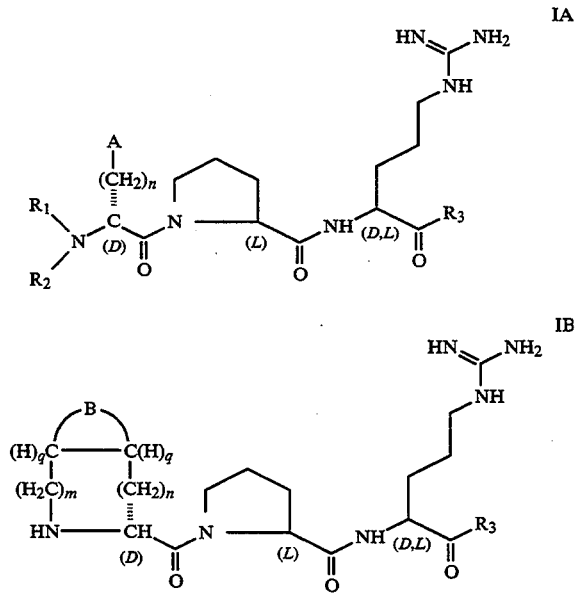

their isomers and mixtures thereof, the hydrates and the pharmaceutically acceptable salts thereof, with the proviso that when $R_1$ and $R_2$ are both H, then $R_3$ is other than $-CF_3$ or $-CF_2CF_3$, wherein m is zero, one or two, n is zero or one, with the proviso that the sum of m and n is less than three and greater than zero, q is zero or one with the proviso that the sum of both q's is zero or 2, $R_1$ is H or $C_{1-7}$ alkyl, $R_2$ is H or $C_{1-7}$ alkyl, or $R_1$ and $R_2$ taken together with the nitrogen atom to which they are attached form a 5- or 6-membered heterocycle, $R_3$ is $-CF_3$, $-CF_2CF_3$, $-CF_2(CH_2)_tCH_3$, $-CF_2(CH_2)_tCOOR_4$, $-CF_2(CH_2)_tCONHR_4$, $-CF_2(CH_2)_tCH_2OR_4$ or $-CF_2(CH_2)_vCH=CH_2$, with t being 2, 3 or 4, and v is 1, 2 or 3, $R_4$ is H or $C_{1-6}$ alkyl, A is phenyl or cyclohexyl, B is $(CH)_4$ or $(CH_2)_4$ which, when taken together with the two carbon atoms to which it is attached, forms a $C_6$-cyclic hydrocarbon moiety.

The natural amino acids, with the exception of glycine, contain a chiral carbon atom. Unless otherwise specifically indicated, the preferred compounds are the optically active amino acids of the L-configuration except, as indicated, it is preferred that Phe be in its D-configuration.

The tripeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, trifluoroacetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid.

An alkyl group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentylmethyl. In the instance wherein $R_1$ and $R_2$ are lower alkyl, it is preferred that one or both be methyl. When $R_1$ and $R_2$ form a 5-6-membered heterocycle with the nitrogen atom to which they are attached the preferred moieties are pyrrolidine and piperidine. Preferred compounds are those wherein at least one of $R_1$ or $R_2$ is methyl.

In the instance of compounds of Formula IA and IB, the $P_1$-α-amino acid residue (arginine) may be in its D- or L-configuration, or a mixture thereof, the $P_2$-α-amino acid residue (proline) preferably is in its L-configuration, and the α-amino acid residue or substituent on the α-carbon atom of the $P_3$ moiety (i.e., the $(CH_2)_nA$ moiety) the residue or substituent preferably is in its D-configuration, and the preferred residue is Phe and the preferred substituent is a cyclohexylmethyl moiety. In the instance of the compounds of Formula IB, the $P_3$ moiety is what is called a "TIC" derivative or "TIC-like" derivative (the expression 37 TIC" being derived from tetrahydroisoquinoline carbonyl). In such instances the bicyclic TIC-moiety formed with the $P_3$ nitrogen atom and the $P_3$-α-carbon atom are of the formulae

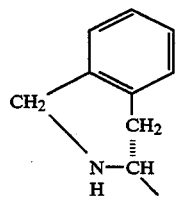

(2a)

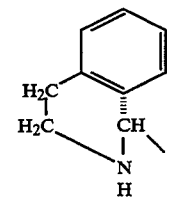

(2b)

3
-continued (2c)

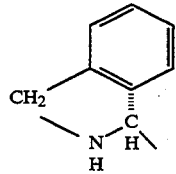

(2'a)

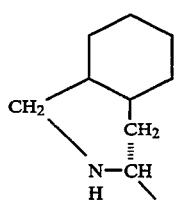

(2'b)

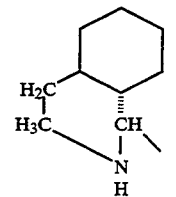

4
-continued (2'c)

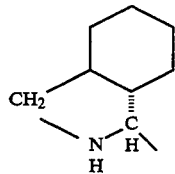

wherein (2a) and (2b) represent a 1,2,3,4-tetrahydroisoquinolinyl moiety, (2'a) and (2'b) represent a 1,2,3,4-decahydroisoquinolinyl moiety, and (2c) and (2'c) represent 2,3-dihydro-1H-isoindolyl and octahydro-1H-isoindolyl moieties, respectively. For convenience the moieties hereinafter may also be referred to as TIC-like modifications.

The compounds of this invention may be prepared by procedures analogously known in the art. In essence the synthesis of the fluorinated alkyl tripeptides of Formula I relies on a modified Dakin-West reaction of 2-phenyl-5(4H) oxazolone and the anhydrides or acyl halides of trifluoroacetic acid, pentafluoropropionic acid or difluoropentenoic acid, (depending on the desired $R_3$ moiety), to yield the requisite polyfluoro alkyl ketone amino acid derivatives for use as key intermediates. Further reactions then allow for the conversion of these amino acid analogs to the desired peptides of Formula I. These reactions are illustrated in the following reaction schemes:

Reaction Scheme A

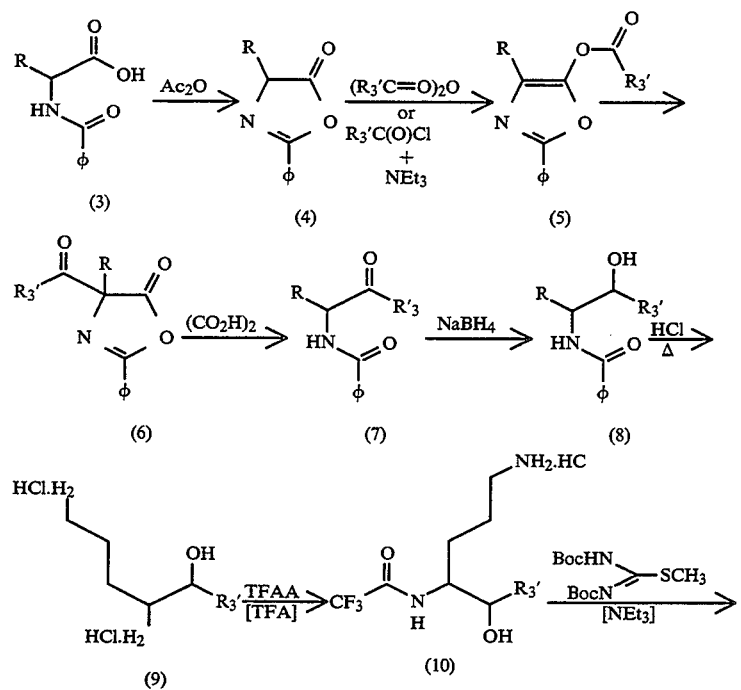

-continued

Reaction Scheme A

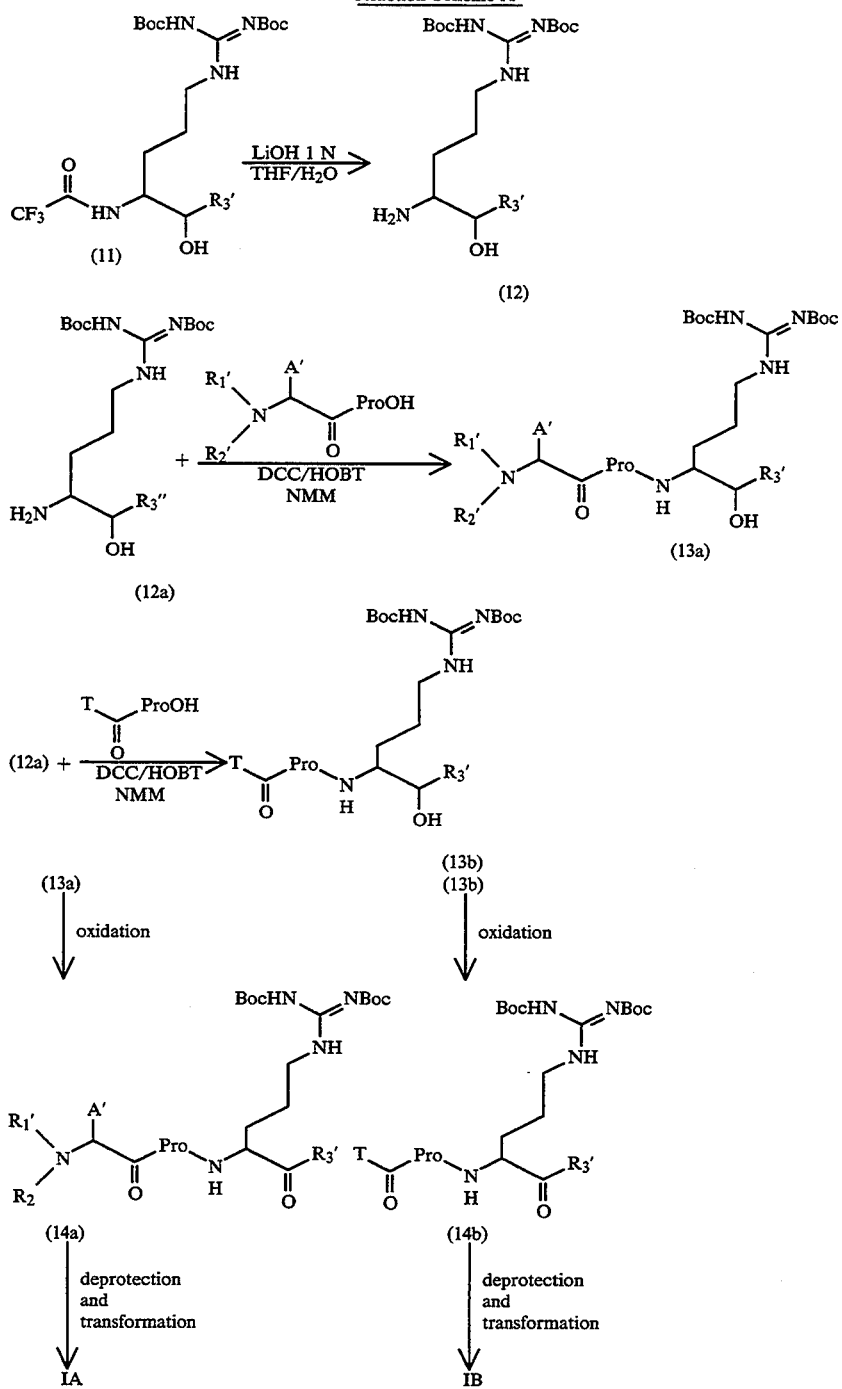

wherein φ is phenyl, A' is . . . (CH$_2$)$_n$A, n is zero or one,

R is φC(O)NH(CH$_2$)$_3$,

R'$_1$ is an N-protecting group,

R'$_2$ is H or C$_{1-7}$ alkyl

R'$_3$ is —CF$_3$, —CF$_2$CF$_3$, —CF$_2$(CH$_2$)$_t$C(O)NHR$_4$, —CF$_2$(CH$_2$)$_t$CH$_2$OR$_4$, or —CF$_2$CH$_2$CH=CH$_2$,

R"$_3$ is —CF$_3$, —CF$_2$CF$_3$, —CF$_2$(CH$_2$)$_t$C(O)NHR$_4$, —CF$_2$(CH$_2$)$_t$CH$_2$OR$_4$ —CF$_2$(CH$_2$)$_v$CH=CH$_2$, or CF$_2$(CH$_2$)$_t$COOR$_4$,

T is a TIC-like moiety as defined above and depicted as 2a, b and c and 2'a, b and c, DCC is dicyclohexylcarbodiimide, NMM is N-methylmorpholine, HOBt is hydroxybenzotriazole (hydrate), TFA is trifluoroacetic acid, TFAA is trifluoroacetic acid anhydride, and A, R$_4$, t, v, Ia and Ib are as previously defined. The preferred amine protecting groups are Boc or CBz and, although the preferred protecting group on the arginine moiety is the depicted Boc group, CBz may also be utilized.

In effecting the foregoing reactions, the N-bis-benzoylated amino acid (3) is cyclized by standard techniques to the 5(4H)-oxazolone (4) (Ac$_2$O, 30 minutes, 90° C. oil bath temperature) in good yield. Evaporation of the solvents affords a highly pure compound which can be used without further purification for the next step. Reaction of the oxazolone (4) using a modified Dakin-West procedure, with the appropriate polyfluoroacid acyl halide (with NEt3) or anhydride, is accomplished at 40° C. (oil bath temperature) under an atmosphere of N2 for 24 hours ($^1$H- and $^{19}$F-NMR-monitoring). When all of the starting material (4) is consumed, the C-4-acylated oxazolones (5) are the main products. Residual anhydride and polyfluorinated acids formed are removed under vacuum (0.01 torr; 25°–70° C. oil bath temperature, acetone/dry ice trap). Alternatively, Compounds (3) may be directly converted to (6) by treatment with the R'3 anhydrides or R'3 acyl halides, and in such instances the intermediates are not isolated. The oily residues are then mixed with a saturated solution of freshly prepared anhydrous oxalic acid in tetrahydrofuran. (Commercial oxalic acid is dried for 16 hours at 100° C. in a drying oven. Two subsequent sublimations (0.01 Torr, 90° C.) afford anhydrous oxalic acid (m.p. 104° C.) which is transferred under an atmosphere of N2 into a flask and stoppered with a septum. Anhydrous tetrahydrofuran is added to the solid until most of it has dissolved (about 4 ml/g) and the resulting solutions are stirred at room temperature for about 16 hours, when gas evolution has completely ceased. Work-up (e.g., EtOAc/H$_{20}$, aqueous NaHCO3, brine; drying over MgSO4) gives in satisfactory yield the desired fluorinated compounds (7) as mixtures of the ketones and their hydrated forms.

For the intended transformation of the α-benzamides (7) the polyfluoroalkyl ketone functionality has to be temporarily masked. This can be achieved by reduction of the ketones (7) (NaBH4:EtOH) to the alcohols (8). The two benzamido functions are cleaved by acid hydrolysis to produce the diaminopolyfluoroalkyl alcohols (9). Regioselective protection of the lateral amino group of the diamino alcohols (9) as a trifluoroacetamide (10) is effected with trifluoroacetic anhydride in trifluoroacetic acid. Guanylation of the ω-amino group into the fully protected arginine analogs (11) is effected with bis-Boc-S-methylisothiourea in triethylamine. Liberation of the lateral-amino protecting function is effected with lithium hydroxide in tetrahydrofuran/water to yield the compounds of Formula (12) which are ready for coupling with the appropriate reactants (i e ,R'$_1$R'$_2$N-CH(A')C(O)ProOH and the TicC(O)ProOH) according to standard procedures well known in the art [Nicolaides, E., DeWald, H., Westland, R., Lipnik, M., and Posler, J., J. Med. Chem. 11, 74 (1968)] to give the completely protected tripeptide alcohol analogs of arginine (13a) and (13b), respectively, which are ready for oxidation of the alcohol function to the corresponding ketones. It is to be noted that compounds (12a) differs in scope from compounds (2) in that it adds the moiety CF2(CH2)$_r$COOR4 to the R'3 moiety Thus, R"3 embraces the R'3 and the CF2(CH2)$_r$COOR4 moieties; the latter being prepared according to Reaction Scheme B.

Although there are several procedures available for the required oxidation, the most preferred method for conversion of (13a) and (13b) to their corresponding ketones (14a) and (14b), the Swern oxidation procedure is most preferred. In general the Swern oxidation [see Synthesis, (1981), 165] is effected by reacting about 2 to 10 equivalents of dimethylsulfoxide (DMSO) with about 1 to 5 equivalents of trifluoroacetic anhydride [(CF3CO)2O] or oxalyl chloride [(COCl)2], said reactants being dissolved in an inert solvent, e.g., methylene chloride (CH2Cl2), said reaction being under an inert atmosphere (e.g., nitrogen or equivalently functioning gas) under anhydrous conditions at temperatures of about −70° C. to −30° C. to form an in situ sulfonium adduct to which is added about 1 equivalent of the appropriate alcohols, i.e., compounds (13a) or (13b). Preferably, the alcohols are dissolved in an inert solvent, e.g., CH2Cl2 or minimum amounts of DMSO, and the reaction mixture is allowed to warm to about −20° C. (for about 10-20 minutes) and then the reaction is completed by adding about 3 to 10 equivalents of a tertiary amine, e.g., triethylamine, N-methyl morpholine, etc.

Another alternative process for converting the alcohols to the desired ketones is an oxidation reaction which employs periodinane (i.e., 1,1,1-triacetoxy-2,1-benzoxiodol), [see Dess Martin, J. Org. Chem., 48, 4155, (1983)]. This oxidation is effected by contacting about 1 equivalent of the alcohols with 1 to 5 equivalents of periodinane (preferably 1.5 equivalents), said reagent being in suspension in an inert solvent (e.g., methylene chloride) under an inert atmosphere (preferably nitrogen) under anhydrous conditions at 0° C. to 50° C. (preferably room temperature) and allowing the reactants to interact for about 1 to 48 hours. Deprotection of the amine protecting groups may be effected as desired after the ketones have been isolated.

Alternatively, a modified Jones oxidation procedure may conveniently be effected by reacting the alcohols with pyridinium dichromate by contacting the reactants together in a water-trapping molecular sieve powder, e.g., a grounded 3 Angström molecular sieve), wherein said contact is in the presence of glacial acetic acid at about 0° C. to 50° C., preferably at room temperature followed by isolation and then removing amine protecting groups.

Alternatively, 1 to 5 equivalents of a chromic anhydridepyridine complex (i.e., a Sarett reagent prepared in situ) [see Fieser and Fieser "Reagents for Organic Synthesis" Vol. 1, pp 145 and Sarett, et al , J.A.C.S. 25, 422, (1953)] said complex being prepared in situ in an inert solvent (e.g., CH2Cl2) in an inert atmosphere under anhydrous conditions at 0° C. to 50° C. to which complex is added 1 equivalent of the alcohols allowing the reactants to interact for about 1 to 15 hours, followed by isolation and removing amine protecting groups. In the special instance wherein R3 is —CF2 (CH2)$_r$COOR4, the procedure for preparing necessary intermediates (corresponding to compounds of Formula (12), but wherein the desired R3 is —CF2(CH2)$_r$COOR4), the reactions of the following reaction scheme may be utilized

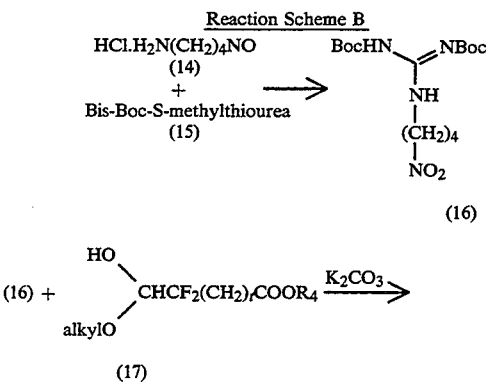

-continued
Reaction Scheme B

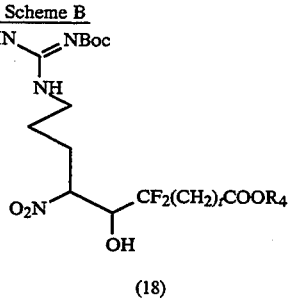

(18)

(18) + H$_2$/Raney Nickel ⎯⎯→

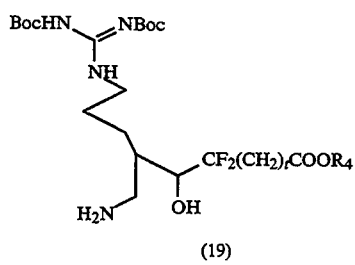

(19)

wherein Boc, R$_4$ and t are as previously defined.

The reactants (17) may be prepared by reacting bromodifluoroethyl acetate [see R. H. Abeles and Ch. P. Govardham, *Archives of Biochemistry and Biophysics*, 280, 137 (1990)] with the appropriate aldehyde, under Reformatsky conditions, to the corresponding difluoro diester alcohols. These alcohols are then mesylated, the mesylated products subjected to elimination by reaction with diazabicycloundecane (DBU) and the so-obtained olefins are reduced by hydrogenation; said mesylation, elimination and hydrogenation being effected by standard and well-known procedures and techniques such as are described in Hing L. Sham et al., *Biochem. and Biophys. Res. Comm.*, 175, 914 (1991). The so-produced intermediates (19), which are incorporated into the structural formula (12a), are then processed as described in Reaction Scheme A.

In the special instance wherein it is desired to prepare compounds wherein R$_3$ is —CF$_2$(CH$_2$)$_2$CH$_3$, the acid anhydride or acyl halide reactants used to prepare compounds of Formula (5) would bear the moiety —CF$_2$CH$_2$CH=CH$_2$ and, when compounds (14a) and (14b) are subjected to transformations, the double bond of the olefins (e.g., —CF$_2$CH$_2$CH=CH$_2$) moiety may also be reduced. In the special instance wherein R$_3$ is CF$_2$(CH$_2$)$_t$CH$_3$ with t being 3 or 4, the corresponding olefins (e.g., CF$_2$CH$_2$CH=CH—CH$_3$ or CF$_2$CH$_2$CH=CHCH$_2$CH$_3$) would be reduced. For the preparation of these latter type olefins, the starting acyl halides or anhydrides can be prepared by the methods described by R. W. Lang et al., *Tetrahedron Letters*, 29, 3291 (1988).

Further processing of the oxidized intermediates [(14a) and (14b)]to the desired compounds of Formulae IA and IB depends essentially on the definition of the R$_1$, R$_2$ and R"$_3$ moieties. In those instances wherein it is desired to prepare final compounds wherein R$_1$ is H and R$_2$ is an alkyl, then the intermediates to be utilized would be those wherein R'$_1$ is a protecting group and R'$_2$ is a C$_{1-7}$ alkyl In such instances the R'$_1$ protecting group and the two protecting groups on the arginine moiety would be removed by techniques well known in the art, such as by reaction with HCl gas/ether or FTA/CH$_2$Cl$_2$. In those instances wherein both R$_1$ and R$_2$ are H, then R'$_1$ would be a protecting group and R'$_2$ would be H and again all three protecting groups (preferably Boc) would be removed as above. In those instances wherein both R$_1$ and R$_2$ are other than H, then R'$_1$ is a protecting group (preferably CBz) and R'$_2$ is H and such intermediates (14a) would be reacted with an appropriate aldehyde (e.g., formaldehyde, glutaraldehyde or succinaldehyde) in the presence of H$_2$/Pd(OH)$_2$/carbon in isopropanol to form the desired N,N-dialkyled, pyrrolidine or piperidine derivatives. The remaining two Boc-protecting groups on the arginine moiety would be cleaved by treatment with HCl Et$_2$O or TFA in CH$_2$Cl$_2$ according to standard techniques well known in the art. In the instance wherein it is desired to convert the olefinic moiety (e.g., a —CF$_2$CH$_2$CH=CH$_2$ moiety) to its saturated analog (e.g., a CF$_2$(CH$_2$)$_2$CH$_3$ moiety), the conversion is effected by standard hydrogenation techniques, preferably concurrently with the removal of the amino-protecting groups.

The following examples illustrate the preparation of the compounds of Formula I.

EXAMPLE 1

L-Prolinamide, N-methyl-D-phenylalanyl-N-[1-[3-[(aminoiminomethyl)amino]propyl]-3,3,3-trifluoro-2-oxopropyl]-, dihydrochloride, hydrate

STEP A

N,N'-bis-Benzoylornithine, ornithuric acid,

A 250 ml flask, equipped with a magnetic stirring barr, two dropping funnels, and a pH-electrode was charged with 3.37 g (20 mmol) of L-ornithine hydrochloride and 40 ml of N NaOH. The stirred solution was cooled to 0° C. and solutions of benzoylchloride (5.0 ml, 44 mmol) in diethylether (50 ml) and of N NaOH (44 ml) were added simultaneously at a rate to keep the pH of the mixture at 12-13. Following complete addition the solution was allowed to warm to room temperature and stirred for further two hours. Diethylether (200 ml) was added, phases separated, and the aqueous layer acidified (pH 0–1, HCl conc.). The white precipitate formed was collected, washed with diethylether and dried (0.01 Torr) to afford 6.7 g (98%) of the title compound. m.p.: 184° C.

$^1$H-NMR (CDCl$_3$, CD$_3$OD 1:1): δ=7.8 (m, 4H, benzoyl), 7.5 (m, 6H, benzoyl), 4.6 (m, 1H, CHN), 3.4 (m, 2H, NCH$_2$), 2.0–1.5 (m, 4H, CH$_2$CH$_2$).

STEP B:

N,N'-[1-(Trifluoroacetyl)-1,4-butanediyl]bis(benzamide), hydrate,

A mixture of the ornithuric acid, as described in Step A, (501.5 g, 1.47 mol) and trifluoroacetic acid (TFAA) (400 ml) was stirred at room temperature for one hour. The resulting solution was evaporated (0.1 Torr) and 1 L of TFAA was added. The solution was stirred for 16 hours and evaporated to dryness (0.01 Torr). Further 1 L of TFAA was added and the solution stirred for 4 hours. Reevaporation of the solution to dryness (0.1 Torr) was followed by addition of further 500 ml of TFAA. The solution was stirred for another 16 hours and evaporated to dryness (0.1 Torr). The oily residue was dissolved in 1.6 L of anhydrous THF and freshly dehydrated oxalic acid (440 g) added to the solution over a period of two hours. Stirring of the mixture was continued for 16 hours, when 7.5 L of ethyl acetate was added. The solution was washed with brine, aqueous sodium bicarbonate (4×), and brine, dried over MgSO$_4$ and evaporated to dryness. Yield of the title compound: 522.8 g (90.5%). Rf =0.33 and 0.27 (eluent: ethyl acetate/petroleum ether 1:1), ketone and its hydrate.

m.p.: 113°–115° C.

$^1$H-NMR (CDCl$_3$) δ=8.0–7.5 (m, 4H, benzoyl), 7.5–7.0 (benzoyl, NH), 6.3 (m, 1H, NH), 5.0 [m, 0.5H, CH(CO)CF$_3$], 4.5 [m, 0.5H, CH(OH)$_2$CF$_3$], 3.4 (m, 2H, NCH$_2$), 2.2–1.6 (m, 4H, CH$_2$CH$_2$).

$^{19}$F-NMR (CDCl$_3$) δ=86.00 (s, COCF$_3$), 80.00 [s, CF$_3$C(OH)$_2$]; ratio 1:1, ketone and hydrate. MS (m/e): 393 (MH+/30% rel. intensity). Analysis calculated for C$_{20}$H$_{19}$F$_3$N$_2$O$_3$H$_2$O (410.40 ): C: 58.53; H: 5.16; N: 6.83. Found: C: 58.62; H: 5.22; N: 6.64.

STEP C

N,N'[1-(2,2,2-Trifluoro-1-hydroxyethyl)-1,4-butanediyl]-bis(benzamide)

NaBH$_4$ (45 g, 1.2 mol) was added portionwise to a cooled (0° C.) and stirred solution of the trifluoromethyl ketone described in Step B, (522 g, 1.33 mol) in 6.5 L of EtOH. The solution was stirred for 10 minutes at 0° C. and then at room temperature for 16 hours. Aqueous HCl (6N) was added and, when effervescence had stopped, solid sodium carbonate was added until the pH of the solution was basic. AcOEt was added and phases separated. The aqueous layer was extracted twice with AcOEt and the combined organic phases washed with brine. Drying of the organic solution (MgSO$_4$) and flash-evaporation (20 Torr, 30° C.) afforded an oil which solidified upon standing. Yield 457.6 g (87%).

m.p.: 103° C., Rf=0.7 (AcOEt).

$^1$H-NMR (CDCl$_3$/CD$_3$OD 1:1): δ=7.9 (m, 4H, benzoyl), 7.4 (m, 6H, benzoyl), 4.4 (m, 1H, CHN), 4.1 (m, 1H, CHCF$_3$), 3.3 (m, 2H, NCH$_2$), 2.0–1.5 (m, 4H, CH$_2$CH$_2$).

$^{19}$F-NMR (CDCl$_3$/CD$_3$OD 1:1) δ=87.33 and 85.83 (2d, J$_{HF}$=7.5 Hz); ratio 3:1.

A small sample (100 mg) was allowed to crystallize for CHN analysis.

Analysis calculated for C$_{20}$H$_{21}$F$_3$N$_2$O$_3$ (394.401): C: 60.76; H: 5.52; N: 7.05. Found: C: 60.55; H: 5.55; N: 7.01.

STEP D 3,6-Diamino-1,1,1-trifluoro-2-hexanol, dihydrochloride

A stirred solution of the N,N'-bis-protected diaminoalcohol described in Step C (457 g) in aqueous HCl 12N (5 L) was heated for 16 hours to reflux. Solvents were evaporated and the oily residue dissolved in H$_2$O. The aqueous solution was washed with diethylether and evaporated to dryness to afford 260 g (87% yield) of the trifluoro-diaminoalcohol, hydrochloride as a slightly colored oil.

$^1$H-NMR (D$_2$O ): δ=4.6 (m, 1H, CHCF$_3$), 3.8 (m, 1H, CHNH), 3.2 (m, 2H, NCH$_2$), 2.0 (m, 2H, CH$_2$CH$_2$).

$^{19}$F-NMR (D$_2$O, C$_6$F$_6$ as ext. ref.): δ=87.3 and 84.8 (2d, J$_{HF}$=7.5 Hz); ratio 3:1.

STEP E

N-[6-[(1,1-Dimethylethoxy)carbonyl]amino]-3-amino-2-hydroxy-1,1,1-trifluorohexane Di-tert-butyldicarbonate (217 g, 0.99 mol) was added portionwise to a cooled (−5° C.) and well stirred solution of the trifluoromethyl-diamino alcohol, dihydrochloride described in Step D (260 g, 1.0 mol) and NEt$_3$ (600 ml, 4.3 mol) in THF/H$_2$O (3 L/3 L). Stirring was continued after complete addition for 1 hour at 0° C. and 16 hours at room temperature. The solution was evaporated to one half of its original volume, acidified (solid citric acid), washed with diethylether, basified (NaOH pellets, pH 12–13), and exhaustively extracted with diethylether. The combined etheral extracts were washed with brine, dried (MgSO$_4$) and evaporated (20 Torr, 30° C.) to afford the ω-protected diamino alcohol.

$^1$H-NMR (CDCl$_3$) δ=4.8 (m, 1H, CHN), 4.0–3.5 (m, 1H, CHCF$_3$), 3.2 (m, 2H, NCH$_2$), 2.5 (m, 3H, exchange with D$_2$O, OH, NH$_2$), 1.8–1.3 (m, 4H, 2CH$_2$), 1.45 (s, 9H, 3CH$_3$).

$^{19}$F-NMR (CDCl$_3$): δ=88.33 and 84.33 (2d, J$_{HF}$=7.5 Hz); ratio 3: 1.

An aliquot (100 mg) was treated with diethylether/methanol (10:1), the solid collected and dried to afford 60 mg of analytically pure above-described compound.

Analysis calculated for C$_{11}$H$_{21}$F$_3$N$_2$O$_3$ (286.301): C: 46.15; H: 7.39; N: 9.78. Found: C: 46.25; H: 7.62; N: 9.46.

STEP F

L-Prolinamide, N-methyl-N-[(phenylmethoxy)carbonyl]-D-phenylalanyl-N-[1-[3-[[(1,1-dimethylethoxy)-carbonyl]amino]propyl]-3,3,3-trifluoro-2-hydroxy-propyl]-

Isobutylchloroformate (2.46 ml, 18.94 mol) was added under an atmosphere of N$_2$ over a period of 10 minutes to a cooled (−20° C.) and stirred solution of N-methyl-N-phenyl-methyloxycarbonyl-D-phenylalanyl-L-proline (7.06 g, 17.22 mol) (S. Bajusz et al., *J. Med. Chem.*, 1990, 33, 1729) and N-methylmorpholine (2.08 ml, 18.94 mol) in anhydrous THF (50 ml). The reaction mixture was stirred for 1 hour at 20° C. and a solution of the ω-N-protected diaminoalcohol described in Step E,(4.92 g, 17.22 mol) in THF (anhydrous, 50 ml) was added. The mixture was stirred for 1 hour at 0° C. and then kept for 16 hours at +4° C. The solvent was evaporated, the residual oil dissolved in AcOEt/H$_2$O, and phases separated. The organic layer was washed with saturated solutions of NaHCO$_3$, citric acid, and brine, dried (MgSO$_4$), and evaporated. The resulting crude tripeptide derivative (15 g, yellow foam) was applied to flash chromatography on silica gel (eluent: AcOEt/hexane 1:1) and the combined product-containing fractions were evaporated (20 Torr, 30° C.; twice with CCl$_4$ as cosolvent, then 0.01 Torr at room temperature, 16 hours) to afford 11.68 g (62%) of the title compound as a colorless foam.

Rf =0.24 (AcOEt/hexane 2:1).

$^1$H-NMR (90 MHz, CDCl$_3$): δ=7.4–7.2 (2m, 10H, 2 aryl), 7.1 (m, 1H, NH), 6.9 (m, 1H, NH), 5.8–5.5 (m, 2H, 2NH), 5.1 (m, 2H, arylCHO$_2$), 4.8–3.5 [6m, 5H, 4CH, OH (exchanges with D$_2$O)], 3.4–2.6 (m, NCH$_3$, 2NCH$_2$, arylCH$_2$), 2.2 and 1.9–1.5 (m,. 8H, 4CH$_2$), 1.4 (m, 9H, 3CH$_3$).

$^{19}$F-NMR (CDCl$_3$): δ=87.1–86.8 (m).

STEP G

L-Prolinamide, N-[(phenylmethoxy)carbonyl]-N-methyl-D-phenylalanyl-1-[3-(aminopropyl)-3,3,3-trifluoro-2-hydroxy-propyl]-, trifluoroacetate A solution of 25 ml of TFA in 25 ml of CH$_2$Cl$_2$ was added to the protected tripeptide derivative described in Step F (7.0 g, 10.32 mol) and the mixture was stirred until effervescence had stopped (30 minutes, bubble counter). The solution was evaporated to dryness (0.01 Torr, 40 hours) to afford a yellow foam. The title compound was precipitated from i.-propanol/petroleum ether to give, after drying, 7.05 g (yield: quantitative) of a white solid.

Rf=0.5 (AcOEt/10% AcOH).

$^1$H-NMR (90 MHz, CD$_3$OD) δ=7.3 (m, 10H, 2 phenyl), 5.1 (m, 2H, CH$_2$O), 4.6–4.45 (m, 1H, CHN-Phe), 4.2 (m, 1H, CHN-Pro), 4.1 (m, 1H, CHN), 3.9 (m, 1H, CHCF$_3$), 3.1–2.6 (m, 9H, NCH$_3$, 3NCH$_2$), 2.0–1.3 (m, 8H, 4CH$_2$).

$^{19}$F-NMR (90 MHz, CD$_3$OD) δ=88.5 (m, CF$_3$CO$_2$H, CF$_3$). Analysis calculated for C$_{30}$H$_{38}$F$_6$N$_4$O$_7$7H$_2$O(710.66): C: 52.38; H: 5.60; N: 7.49. Found: C: 52.59; H: 5.60; N: 7.49.

STEP H

L-Prolinamide, N-[(phenylmethoxy)carbonyl]-N-methyl-D-phenylalanyl-N-1-[3-[[bis[[(phenylmethoxy)carbonyl]amino]-methylene]amino]propyl]-3,3,3-trifluoro-2,-hydroxypropyl]

N,N'-bis-Benzyloxycarbonyl-S-methylisothiourea (3.46 g, 9.7 mol) was added under an atmosphere of N$_2$ to a solution of the trifluoroacetate salt described in Step G (5.57 g, 8 mol) and NEt$_3$ (1.67 ml), in 50 ml of anhydrous THF. The solution was stirred at 40° C. for 4 days. THF was evaporated and the solid residue dissolved in Et$_1$O. The etheral solution was washed with a saturated solution of citric acid and brine, dried (MgSO$_4$), and solvents evaporated. The solid residue was applied to a flash chromatography column charged with silica gel (230–400 mesh, eluent AcOEt/hexane 1:2) and when all residual isothiourea (Rf=0.8) had sorted AcOEt/hexane 1:1–2:1 and the combined product-containing fractions were evaporated to afford 5.08 g (71% yield) of the guanidino tripeptide derivative as a colorless foam.

Rf=0.3 (AcOEt/hexane 2:1).

$^1$H-NMR (360 MHz, CDCl$_3$): δ=11.5 (s, broad, 1H, ZNH guanidine), 8.3 (m, 1H, NH guanidine), 7.3–7.2 (m, 22H, 4 phenyl, 2NH), 5.7 (m, 1H, NH), 5.1 (m, 7H, NH, 3CH$_2$O), 4.8–3.9 (m, 5H, CHN-Phe, CF$_3$CHO, CHN-Pro, CHN, NH), 3.8–2.5 (m, 9H, NCH$_2$-Pro, NCH$_2$ guanidine NCH$_3$, CH$_2$-Phe), 1.8–1.5 (m, 8H, 4CH$_2$).

$^{19}$F-NMR (360 MHz, $^1$H-decoupled, CDCl$_3$): δ=87.49, 87.12, 87.00 and 85.16 (4s). Analysis calculated for C$_{46}$H$_{51}$F$_3$N$_6$O$_9$. 0.5 H$_2$O (897.96): C: 61.53; H: 5.84; N: 9.36. Found: C: 61.53; H: 5.75; N: 9.27.

STEP I

L-Prolinamide, N-[(phenylmethoxy)carbonyl]-N-methyl-D-phenylalanyl-N-[1-[3-[[bis [[(phenylmethoxy)carbonyl]amino]methylene ]amino]propyl]-3,3,3trifluoro,2-oxopropyl], dihydrate A 250 ml three necked flask, equipped with a magnetic stirring barr, thermometer, and an N$_2$ inlet was charged with a solution of oxalylchloride (0.74 ml, 8.4 mmol) in 10 ml of anhydrous CH$_2$Cl$_2$ and placed in a dry-ice/acetone bath (×55° C. internal temperature). A solution of DMSO (1.2 ml, 17 mmol) in 200 ml of CH$_2$Cl$_2$ was added under an atmosphere of N$_2$ at a rate to keep the internal temperature at −55° C. Stirring was continued for 5 minutes and a solution of the alcohol described in Step H (4.98 g, 5.6 mmol) in 10 ml of CH$_2$Cl$_2$ was added in one portion. The mixture was allowed to warm to −25° C. and stirred at that temperature for 10 minutes. The solution was cooled again to −55° C., 3.9 ml of NEt$_3$ was added slowly, and the ice bath removed. When the internal temperature had reached −20° C. a saturated solution of citric acid was added. 250 ml of CH$_2$Cl$_2$ were added at room temperature, phases separated and the organic layer washed with H$_2$O, a saturated solution of NaHCO$_3$, and brine. Drying (MgSO$_4$) and evaporation of the solvents afforded 5.07 g of a yellow oil. Flash chromatography on silica gel (230–400 mesh, eluent AcOEt/hexane 1:1) and evaporation of the combined product-containing fractions gave 3.71 g (74%) of the ketone as a colorless foam.

Rf=0.5 (AcOEt/hexane 2:1).

$^1$H-NMR (CDCl$_3$) δ=11.5 (broad s, 1H, NH-Z), 8.5 (m, 1H, NH guanidine), 7.3 (m, 20H, 4 phenyl), 5.7 (3m, 1H, NH), 5.1 (m, 6H, 3CH$_2$O), 4.8 (m) and 4.7–4.2 (m, 4H, 4CH), 3.9 (m) 3.7-3.3 (m) and 2.6 (m, 9H, NCH$_2$-Pro, NCH$_2$ guanidine, NCH$_3$, arylCH$_2$), 2.0–1.5 (m, 8H, 4CH$_2$).

$^{19}$F-NMR (CDCl$_3$): δ=86.08, 85.96, 85.88 and 85.83 (4s). Analysis calculated for C$_{46}$H$_{49}$F$_3$N$_6$O$_9$. H$_2$O (913.95): C: 60.45; H: 5.74; N: 9.20. Found: C: 60.52; H: 5.56; N: 9.16.

STEP J

L-Prolinamide,N-methyl-D-phenylalanyl-N-[1[3-[(aminoiminomethyl)amino]propyl]-3,3,3-trifluoro-2-oxopropyl]-, dihydrochloride, hydrate A solution of the ketone described in Step I (2.94 g, 3.3 mmol) in 100 ml of isopropanol, 15 ml of HCl 1N, and 0.5 g of Pd(OH)$_2$/C (10%, Pearlman's catalyst) was hydrogenated under atmospheric pressure for 4 days. Evaporation of the solvent left an oily residue which was dissolved in water. The aqueous phase was washed with ether and lyophilized to give 0.665 g (62% yield) of the title compound as a white powder.

Rf=0.5, AcOH/BuOH/H$_2$O 1/3/1.

$^1$H-NMR (D$_2$O): δ=7.4 and 7.3 (2m, phenyl), 4.45, 4.35 and 4.2[3m, 2H, NCHCO, CHC(OH)$_2$CF$_3$], 3.5–3.1 and 2.8 (3m, 6H, NCH$_2$ guanidine, NCH$_2$-Pro, CH$_2$-Phe, NCH$_3$), 2.2–1.4 (m, 8H, 4CH$_2$), 2.0 (s, CH$_3$CO$_2$H).

$^{19}$F-NMR (D$_2$O): δ=-6.16 and -6.34 [2s, ratio 55.45, CF$_3$C(OH)$_2$].

By substituting the TFAA reactant used in Step B of this example with equivalent quantities of pentafluoropropionic anhydride (PFPAA), and by substantially following the procedures of Steps B to J, there was produced L-Prolinamide, N-methyl-D-phenylalanyl-N-[1-[3-[(aminoiminomethyl)amino]propyl]-3,3,4,4,4-pentafluoro-2-oxobutyl]- (see Example 6, Steps A to J).

EXAMPLE 2

L-Prolinamide, N-D-(phenylalanyl-N-[1-[3-[(amino)iminomethyl)amino]propyl]-3,3,3-trifluoro-2-oxopropyl]-, hydrofluoride, acetate, hydrate

STEP A

L-Prolinamide, N-[(phenylmethoxy )carbonyl]-D-phenylalanyl-N-[1-[3-[(1,1-dimethylethoxy)carbonyl]amino]propyl-3,3,3-trifluoro-2-hydroxypropyl]

Isobutylchloroformate (0.450 ml, 3.46 mmol) was added under an atmosphere of N$_2$ to a cooled (−10° C.) and stirred solution of phenylmethyloxycarbonyl-D-phenylalanyl-L-proline (Z-D-Phe-Pro-OH, 1.27 g, 3.2 mmol) and N-methylmorpholine (0.38 ml, 3.46 mmol). The reaction mixture was stirred for 10 minutes at −10° C. and a solution of the ω-N-protected diaminoalcohol of Step E of Example 1 (0.9 g, 3.19 mmol in tetrahydrofuran (anhydrous, 6 ml) was added. The mixture was stirred for 1 hour at 0° C. and then kept for 16 hours at +4° C. AcOEt/H₂O (100 ml each) was added and phases separated. The organic layer was washed with saturated solutions of NaHCO₃, citric acid, and brine (each 3×50 ml), dried over MgSO₄, and evaporated. The resulting crude tripeptide derivative (2.5 g, yellow foam) was applied to flash chromatography (silica gel, 100 g, eluent: AcOEt/hexane 1:1) and the combined product-containing fractions were evaporated (20 Torr, 30° C.; twice with CCl₄ as cosolvent, then 0.01 Torr, room temperature, 16 hours) to afford 1.5 g (72%) of the title compound as a colorless foam.

Rf=0.14 (AcOEt/hexane)

¹H NMR (360 MHz, CDCl₃) δ=7.4–7.2 (3 m, 10H, 2 aryl), 7.1 (m, 1H, NH), 5.8–5.5 (m, 2H, 2NH), AB centered at 5.10 ($J_{HA-HB}$=10 Hz, 2H, arylCH₂O), 4.8–3.5 [6 m, 5H, 4CH, OH (exchanges with D₂O)], 3.2–2.9 and 2.6 (2 m, 6H, 2NCH₂, aryl, CH₂), 2.2 and 1.9–1.5 (m, 8H, 4CH₂), 1.4 (m, 9H, 3CH₃).

¹⁹F-NMR (CDCl₃): δ=87.1; 86.8 (2 d, $J_{HF}$=7.5 Hz), 86.5 (m), 85.2; 85.1 (2 d, $J_{HF}$=7.5 Hz), 85.0 (m). MS (CI/NH₃): m/e=665 (MH+, 50%). Analysis calculated for C₃₃H₄₃F₃N₄O₇0.4 CCl₄ (726.258): C 54.94, H 5.97, N 7.71 Found: C 54.74, H 6.12, N 7.29.

STEP B

L-Prolinamide, N-[(phenylmethoxy)carbonyl]-D-phenylalanyl-N-[1-[(3-amino)propyl]-3,3,3-trifluoro-2-hydroxypropyl]-, trifluoroacetate, hydrate A solution of 5 ml TFA in 5 ml of CH₂Cl₂ was added to the protected tripeptide derivative (1.39 g, 2.09 mmol) and the mixture was stirred until effervescence had stopped (20 min, bubble counter). The solution was evaporated to dryness (0.01 Torr, 40 hours). An aliquot (0.68 g) was taken from the resulting yellow foam, 100% for the following reaction, and the rest treated with i-propanol/hexane to afford 0.73 g of the title compound as a white solid.

Rf=0.5 (AcOEt/10% AcOH).

¹H-NMR (360 MHz, CD₃OD): δ=7.3 (m, 10H, 2 phenyl), AB's centered at 5.1 ($J_{HA-HB}$=23 Hz, 2H, CH₂O), 4.6 (t, J=7.5 Hz, 0.5H), and 4.45 (dd, J=7.5 Hz, 0.5H, 1H, CHCF₃), 2.9 and 2.6 (2 m, 6H, 3NCH₂), 2.0–1.3 (m, 8H, 4CH₂).

¹⁹F-NMR (360 MHz, CD₃OD): δ=88.48 (s, CF₃CO₂H), 88.35, 88.20, 87.21, and 87.18 (4 d, $J_{HF}$=7 Hz, CF₃); ratio 16:10:3:3. MS (CI/NH₃): m/e=565 (MH+, 100% rel. intensity). Anal. calcd. for C₃₀H₃₆F₆N₄O₇ . 0.5 H₂O (687.64): C 52.40, H 5.42, N 8.15. Found: C 52.30, H 5.69, N 7.83.

STEP C

L-Prolinamide, N-[(phenylmethoxy)carbonyl]-D-phenylalanine-N-[1-[3-[[bis-[[(1,1-dimethylethoxy)carbonyl]amino]methylene]amino]propyl]-3,3,3trifluoro-2-hydroxypropyl]-

N,N'-Bis-Boc-S-methylisothiourea [Bergeron, R. J. and McManis, J. S., *J. Org. Chem.*, 1987, 52, 1700](1.40 g, 4.83 mmol) was added under an atmosphere of N₂ to a solution of the trifluoroacetate salt (12) (0.82 g, 1.2 mmol) and NEt₃(0.25 ml, 1.81 mmol) in 4 ml of anhydrous tetrahydrofuran. The solution was stirred at 40° C. for 4 days. Tetrahydrofuran was evaporated and the solid residue dissolved in Et₂O. The ethereal solution was washed with a saturated solution of citric acid and brine, dried (MgSO₄), and solvents evaporated. The solid residue was applied to a flash chromatography column charged with silica gel [30 g, 230–400 mesh, eluent AcOEt/hexane 1:2 and when all residual isothiourea (Rf=0.8) had sorted AcOEt/hexane 1:1–2:1]and the combined product-containing fractions were evaporated to afford 0.44 g (45%) of the expected quanidino tripeptide derivative as a colorless foam.

Rf=0.3 (AcOEt/hexane: 2:1).

¹H-NMR (360 MHz, CDCl₃): δ=11.5 (s, broad, 1H, BocNH guanidine), 8.3 (m, 1H, NH guanidine), 7.2 (m, 11H, 2 phenyl, NH), 6.0, 5.9, and 5.7 (3 m, 1H, NH), AB's centered at 5.1 (J=23 Hz, 2H, CH₂O), 4.4 (m, 1H, CHN-Phe), 4.3–3.2 (6 m, 7H, CHN-Pro, NCH₂-Pro, NCH₂ guanidine A-part, CHCF₃, OH), 3.0 (m, 2H, aryl CH₂), 2.6 (m, 1H, NCH₂ guanidine B-part), 1.8–1.2 (m, 26H, 6CH₃, 4CH₂).

¹⁹F-NMR (360 MHz, CDCl₃): δ=86.95, 86.86, 85.39, and 85.16 (4 d, $J_{HF}$=7 Hz); ratio 5:5:1:1.5. Anal. calcd. for C₃₉H₄₃F₃N₉O₆.H₂O (824.88): C 56.79, H 6.72, N 10.19. Found C 56.53, H 6.54, N 10.05.

STEP D

L-Prolinamide, N-[(phenylmethoxy)carbonyl]-D-phenylalanyl-N-[1-[3-[[bis-[[(1,1-dimethylethoxy)carbonyl]amino]methylene]amino]propyl]-3,3,3trifluoro-2-oxopropyl]-, hydrate A 25 ml three necked flask, equipped with a magnetic stirring barr, thermometer, and an N₂ inlet was charged with a solution of oxalylchloride (0.127 g, 1 mmol) in 1 ml of anhydrous CH₂Cl₂ and placed in a dry ice/acetone bath (−55° C. internal temperature). A solution of DMSO (0.22 g, 2.8 mmol) in 1 ml of CH₂Cl₂ was added under an atmosphere of argo₂ at a rate to keep the internal temperature at −55° C. Stirring was continued for 5 minutes and a solution of the alcohol described in Step C (0.4 g, 0.5 mmol) in 2 ml of CH₂Cl₂ was added in one portion. The mixture was allowed to warm to −25° C. and stirred at that temperature for 10 minutes. The solution was cooled again to −55° C., 0.5 ml of NEt₃ was added slowly, and the ice bath removed. When the internal temperature had reached −20° C. a saturated solution of citric acid was added. 50 ml of CH₂Cl₂ were added at room temperature, phases separated and the organic layer washed with water, a saturated solution of NaHCO₃, and brine. Drying over MgSO₄and evaporation of the solvents afforded 0.34 g of a yellow oil. Flash chromatography on silica gel (0.01 g, 230–400 mesh, eluent AcOEt/hexane 1:1, then 2:1) and evaporation of the combined product-containing fractions gave 0.24 g (60%) of the expected ketone as a colorless foam.

Rf=0.5 (AcOEt/hexane: 2:1).

¹H-NMR (CDCl₃): δ=11.5 (s, broad, 1H, BocNH), 8.5 (m, 1H, NH guanidine), 7.3 (m, 10H, 2 phenyl), 5.7 (3 m, 1H, NH), 5.1 (m, 2H, CH₂O), 4.8 (m) and 4.7–4.2 (m, 4H, 4CH), 3.9 (m) 3.7–3.3 (m) and 2.6 (m, 4H, NCH₂-Pro, NCH₂ guanidine), 3.0 (m, 2H, aryl CH₂), 2.0–1.4 (m, including s at 1.5, 26H, 6CH₃, 4CH₂).

¹⁹F-NMR (CDCl₃,H-decoupled): δ=86.14 and 85.89 (2 d, ratio 1:2, CF₃CO), 80.22 and 79.69 [2s, ratio 1:1, CF₃C(OH)₂].

¹³C-NMR (CDCl₃): δ=175.5–174.29 (4s, CONH), 164.1 (2s), 158.8–156.8 (4s) and 153.9 (s, OCON, OCON=C), 136.5 and 136.2 (2s, phenyl), 130.8–128.0 (8s, phenyl), 125.57, 122.38, and 121.19 (visible part of q, $J_{CF}$=107.6 Hz, CF₃), 95.4–94.7 [4s, C(OH)₂], 83.8–83.7 (3s) and 80.0, 79.9 (2s, C), 68.2–67.8 (3s, CH₂O), 61.5–59.4 (2s, NCH-Pro), 55.6–54.4 (several s, NCH-Phe, NCH COCF₃), 47.87 and 47.65 (2s, NCH₂-Pro), 41.0–40.7 (2s, NCH₂ guanidine), 39.11–38.48 (2s, phenyl CH₂), 31.8–24.6 (several s, CH₂-Pro, 2-tert-butyl, CH₂ guanidine, CH₂-Pro). Anal. calcd. for $C_{39}H_{51}F_3N_6O_9 \cdot 2H_2O$ (840.86): C 55.71, H 6.59, N 9.99. Found C 55.75, H 6.25, N 9.78.

STEP E

L-Prolinamide, N-D-phenylalanyl-N-[1-[3-[(aminoiminomethyl)amino]propyl]-3,3,3-trifluoro-2-oxopropyl]-, hydrofluoride, acetate, hydrate The reaction flask of a "Sakakibara apparatus" was charged with 0.1 g (0.119 mmol) of the ketone of Step D and applied to liquid HF deprotection of all protecting groups. After a reaction time of 20 minutes HF was evaporated, the solid residue dissolved in a mixture of AcOH/$H_2O$ 1:1, and lyophilized. The solid residue was dissolved in water, the mixture filtered through a Millipore® filter, and lyophilized again to afford 40 mg (57%) of the title compound as a solid.

$^1$H-NMR ($D_2O$): δ=7.4 and 7.3 (2 m, phenyl), 4.45, 4.35 and 4,2 [3 m, 2H, NCHCO, CHC(OH)$_2$CF$_3$], 3.5–3.1 and 2.8 (3 m, 6H, NCH$_2$ guanidine, NCH$_2$-Pro, CH$_2$-Phe), 2.2–1.4 (m, 8H, 4CH$_2$), 2.0 (s, CH$_3$CO$_2$H).

$^{19}$F-NMR (CD$_2$O): δ= −2.91 (s,.CF$_3$CO), −6.16 and −6.34 [2s, ratio 55:45, CF$_3$C(OH)$_2$], −54.28 (s, F$^-$=1.5 HF/CF$_3$. Analysis calculated for $C_{21}H_{29}F_3N_6O_3 1.5$ HF. .0.5 $CH_3CO_2H$.3 $H_2O$ (584.58): C 45.20, H 6.64, N 14.38. Found C 55.75, H 6.25, N 9.78.

By substituting the TFAA reactant of Step B of Example 1 with equivalent amounts of PFPAA and by following Steps B, C, D and E of Example 1, and using the product of that reaction in Step A of this example and by following the teachings of Steps B, C, D and E of this example, there was produced L-prolinamide, N-[1-[3-[(aminoiminomethyl)amino]propyl]3,3,4,4,4-pentafluoro-2-oxobutyl]-, hydrofluoride, hydrate.

EXAMPLE 3

L-Prolinamide, N,N-dimethyl-D-phenylalanyl,N-[1-[3-[(amino-iminomethyl)amino]propyl]-3,3,3-trifluoro-2-oxopropyl]-, dihydrochloride, hydrate

STEP A

L-Prolinamide, N,N-(dimethyl)amino-D-phenylalanyl-N-[1-[3-[[bis- [[(1,1-dimethylethoxy)carbonyl]amino]-methylene]amino]propyl]-3,3,3-trifluoro-2-oxopropyl]-, hydrate An aqueous solution of formaldehyde (37%, 24 μl) was added to a suspension of the fully protected ketone (product of Step D, Example 2, 0.822 g, 1 mmol) in isopropanol (10 ml) and 200 mg of the catalyst Pd(OH)$_2$ on carbon. The resulting suspension was hydrogenated under atmospheric pressure until hydrogen uptake was stopped (≃24 hours). Filtration from the catalyst afforded a slightly yellow solution which was evaporated to one third of its original volume. The residue was diluted with 10 ml of water and the solution lyophilized to give a yellow foam which was used as such in the next step.

Step B L-Prolinamide, N,N-dimethyl -D-phenylalanyl-N-[1-[3-[(aminoiminomethyl)amino]-propyl]-3,3,3-trifluoro-2-oxopropyl]-, dihydrochloride r hydrate To a suspension of the above-prepared ketone (0.72 g, 1 mmol) in anhydrous ether (10 ml) was added a saturated solution of HCl-gas in anhydrous ether (4M, 50 ml). Stirring of the mixture for 2 days and evaporation of the solvents afford the title compound as a slightly yellow foam (0.60 g).

Rf=0.5, (BuOH/AcOH/$H_2O$: 3/1/1).

By substituting the formaldehyde reactant of Step A of Example 3 with equivalent amounts of succinaldehyde or glutaraldehyde and by following the processes of Steps A and B, there was produced the pyrrolidine and piperidine analogs, respectively, of the dimethyl-D-Phe compound of Example 3, (i.e., the corresponding salts of

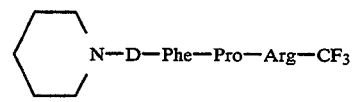

and

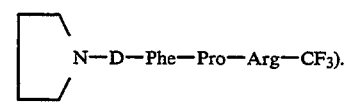

Similarly, by substituting the trifluoroacetic anhydride (TFAA) of Step B of Example 1 with equivalent amounts of pentafluoropropionic anhydride (PFPAA) and by following the teachings of Examples 1 to 3 there was produced the corresponding pentafluoropropionyl analogs [i.e., the salts of compounds (a) (CH$_3$)$_2$N-D-Phe-Pro-Arg-CF$_2$CF$_3$, (b)
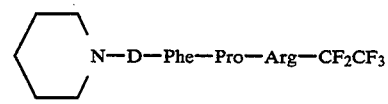

and

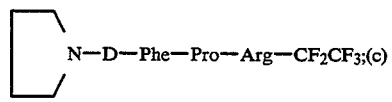

it being noted that the nitrogen atom of the depicted pyrrolidine and piperidine moieties was the terminal nitrogen atom of the D-phenylalanine α-amino acid.

EXAMPLE 4

L-Prolinamide, N[1-[3-[(aminoiminomethyl)amino]-propyl]-3,3,4,4,4-pentafluoro-2-oxobutyl]-1-D-[(1,2,3,4-tetrahydro-3-isoquinolinyl)carbonyl]-, dihydrochloride, hydrate

STEP A

N-(1,1-Dimethylethoxy)carbonyl-D-1,2,3,4-tetrahydro-3-isoquinoline carboxylic acid Di-tert-butyldicarbonate [(Boc)$_2$O, 6.78 g, 31.0 mmol, 1.1 and eq.] and NEt$_3$ (4.33 ml, 31.0 mmol, 1.1 eq) were added to a solution of D-3-TIC (5.00 g, 28.2 mmol) in a mixture of water (55 ml) and THF (55 ml). The mixture was stirred at room temperature for 12 hours. After evaporation of THF, the aqueous phase was washed twice with Et$_2$O, acidified with a saturated solution of citric acid and extracted three times with AcOEt. The combined organic phases were washed with brine, dried over MgSO$_4$ and evaporated. The residue was dried at reduced pressure (0.01 Torr) to afford the protected amino acid as white foam. Yield 7.32 g, (94%). m.p.: 104°–105° C., Rf=0.7 (AcOEt/AcOH=98:2). MS ($C_{15}H_{19}NO_4$=277): (CI/NH$_3$): m/e=278 (MH$^+$, 40%); 239 (90%); 222 [MH+ −56, MH+ +H₂C=C(CH₃)₂, 90%]; 178 (MH+ −100, MH+ −Boc, 100%).

¹H-NMR: (CDCl₃, 90 MHz): δ=9.8 (broad s, 1H, COOH); 7.12 (s, 4H, C₆H₄); 5.0 (0.5H) and 4.77 (s, 0.5H, NCH); 4.56 (d, J=9.0 Hz, 2H, NCH₂); 3.12 (m, 2H, CH₂); 1.4 (broad s, 9H, Boc).

STEP B

N,(1,1-Dimethylethoxy)carbonyl-D-1,2,3,4-tetrahydro-3-isoquinolinyl-L,proline-benzylester DCC (5.38 g, 26.1 mmol, 1.0 eq.) was added to a cooled and stirred solution (0° C.) of Boc-D-3-TIC (Step A, 7.22 g, 26.1 mmol) and HOBt (3.98 g, 26.1 mmol, 1.0 eq.) in CH₂Cl₂ (200 ml). The mixture was stirred at 0° C. during 30 minutes, and then L-Pro-benzylester hydrochloride (6.30 g, 26.1 mmol, 1.0 eq.) and NMM (3.10 ml, 28.7 mmol, 1.1 eq.) were added. The solution was stirred at room temperature during 12 hours. After filtration of the DCU, the filtrate was evaporated. The resulting residue was then dissolved in AcOEt and refiltered. The filtrate was washed twice with saturated solutions of NaHCO₃, citric acid, and then once with water and brine, dried over MgSO₄ and evaporated. After drying at reduced pressure (0.01 Torr), the protected dipeptide was obtained as a white foam. Yield: 9.69 g (80%). m.p.: 93°–95° C., Rf=0.5 (petroleum ether/AcOEt=2/1) MS (C₂₇H₃₂N₂O₅=464): m/e=465 (MH+, 100%); 365 (MH+ −100, MH+ −Boc, 40%); 257 [MH+ −208, MH+ −(Boc+OBn), 50%]; 225 (40%); 206 (30%).

¹H-NMR: (CDCl₃, 90 MHz): δ=7.4–7.1 (m, 9H, C₆H₄, C₆H₅); 5.2–4.3 (m, 4H, NCH₂-TIC, N—CH-TIC, NCH-Pro); 5.0 (broad s, 2H, OCH₂); 3.5 (m, 2H, NCH₂-Pro); 3.0 (m, 2H, CH₂-TIC); 1.9 (m, 4H, 2CH₂-Pro); 1.40 (s, 9H, Boc).

STEP C

N-(1,1-Dimethylethoxy)carbonyl-D-1,2,3,4-tetrahydro-3-isoquinolinyl-proline

Palladium hydroxyde on carbon (20%, Pd(OH)₂C, Pearlman's catalyst) was added to a solution of Boc-D-3-Tic-L-Pro-benzylester (Step B) (9.69 g, 20.9 mmol) in isopropanol (150 ml). The mixture was hydrogenated at atmospheric pressure and at room temperature for 12 hours during which the acid precipitates. MeOH (100 ml) was added and the solution was filtered over celite and the filtrate evaporated. The solid residue was washed with Et20 and then with petroleum ether. The Boc-protected dipeptide was obtained upon drying at reduced pressure (0.01 Torr) as a white solid. Yield: 6.60 g (85%).

m.p.: 216°–218° C. (decomposed), Rf=0.75 (BuOH-/AcOH/H₂O=3:1:1)

MS (C₂₀H₂₆N₂O₅=374): (CI/NH₃): m/e=375 (MH+, 50%); 275 (MH+ −Boc, 22%), 257 [MH+ −(Boc+H₂O), 100%]Analysis calculated for C₂₀H₂₆N₂O₅; 0.25 H₂O (378.9): C: 63.39; H: 7.05; N: 7.39 Found: C: 63.54; H: 6.94; N: 7.49. [α]$_D^{20}$: −15.5 (C=1, MeOH).

¹H-NMR: (CD₃OD, 360 MHz): δ=7.2 (broad s, 4H, C₆H₄); 5.2 and 4.9 (2 m, 1H, NCH-TIC); 2 AB systems centered at 4.58 {[A: 4.75 (J=16 Hz); B: 4.43 (J=16 Hz)], 2H, NCH₂—TIC)}; 4.3 (m, 1H, NCH-Pro); 3.9–3.4 (m, 2H, NCH₂); 3.3–2.9 (m, 2H, CH₂-TIC); 2.3–1.9 (2 m, 4H, 2CH₂); 1.5 (broad s, 9H, Boc).

STEP D

L-Prolinamide, N-[1-[3-[[bis[[(1,1-dimethylethoxy)-carbonyl]amino]methylene]amino]propyl]-3,3,4,4,4-pentafluoro-2-hydroxybutyl]-1-[(1,1-dimethylethoxy)carbonyl]-D-[(1,2,3,4-tetrahydro-3-isoquinolinyl)carbonyl]

DCC (0.255 g, 1.2 mmol, 1.0 eq.) was added to a cooled and stirred solution (0° C.) of Boc-D-3-Tic-Pro (0.462 g, 1.2 mmol) and HOBt (0.189 g, 1.2 mmol, 1.0 eq.) in CH₂Cl₂ (15 ml). The mixture was stirred at 0° C. during 30 minutes, when the amino alcohol (12) (Reaction Scheme A) (0.59 g, 1.2 mmol, 1.0 eq.) and NMM (0.15 ml, 1.4 mmol, 1.1 eq.) were added. The solution was stirred at room temperature during 12 hours. The mixture was filtered from the precipitated DCU. The filtrate was washed with saturated solutions of citric acid, KHCO₃ and brine, dried over MgSO₄, and evaporated. The resulting residue was applied to flash chromatography on silica gel (eluent: petroleum ether-/AcOEt: 3/2. The tripeptide alcohol analog was isolated as a white solid. Yield: 0.62 g (85%).

m.p.: 102°–104° C., Rf=0.3 (petroleum ether/AcOEt=1:1)

MS (C₃₈H₅₅N₆O₉F₅=834): (CI/NH₃): m/e=635 (MH+ −200, MH+ −2 Boc 100%); 593 [MH+ −242, MH+ −(2 Boc+N≡CNH₂), 50%]; 535 (MH+ −300, MH+ −3 Boc, 15%)

¹H-NMR: (CDCl₃, 360 MHz): δ=11.5; 8.4 and 7.5 (broad 3s, 3H, 3NH); 7.2 (m, 4H, C₆H₄); 5.1 and 4.8 (broad 2s, 1H, NCH-TIC); 4.80 (d, J=11.8 Hz, 2H, NCH₂-TIC); 4.7–4.4 (m, 2H, NCH-Pro, CF₂CH); 4.3–3.7 (m, 3H, NHCH, NCH₂-Pro); 3.6–3.5; 3.5–3.3 and 3.1–3.0 (3 m, 5H, 2CH₂, OH); 2.4–1.6 (m, 8H, 4CH₂); 1.5 (broad s, 27H, 3 Boc).

¹⁹F-NMR: (CDCl₃, C₆F₆ ext. ref., 360 MHz): δ=79.12; 78.94; 78.90 and 78.74 (4s, 3F, CF₃, 2 diastereoisomers and 2 isomers cis/trans: ratios=5:7.5: 1.5:1); ABX system centered at 35.98 [A: 40.57 (J$_{FA-FB}$=280 HZ); B: 31.39 (J$_{FB-FA}$=280 Hz; J$_{FB-HX}$=30 Hz)]; ABX system centered at 35.82 [A: 39.84 (J$_{FA-FB}$=280 Hz); B: 32.30 (J$_{FB-FA}$=280 Hz; J$_{FB-HX}$=30 Hz)]; ABX system centered at 33.95 [A: 39.18 (J$_{FA-FB}$=280 Hz); B: 28.72 (J$_{FB-FA}$=280 Hz; J$_{FB-HX}$=30 Hz)]; ABX system centered at 34.41 [A: 39.18 (J$_{FA-FB}$=280 Hz); B: 29.64 (J$_{FB-FA}$=280 Hz; J$_{FBHX}$=30 Hz)];2F, CF₂, 2 diastereoisomers and 2 isomers cis/trans: ratios: 7.5:5:1.5:1).

Step E

L-Prolinamide, N-[1-[3-[[bis-[[(1,1-dimethylethoxy)carbonyl]-amino]methylene]amino]propyl]-3,3,4,4,4-pentafluoro-2-oxobutyl]-1-[(1,1-dimethylethoxy)carbonyl]-D-[(1,2,3,4-tetrahydro-3-isoquinolinyl)carbonyl]

A solution of oxalyle chloride (0.122 ml, 1.4 mmol, 2.0 eq.) in 3 ml of anhydrous CH₂Cl₂ was cooled under N₂ to −60° C. A solution of dimethylsulfoxide (0.197 ml, 2.8 mmol, 4.0 eq.) in 6 ml of anhydrous CH₂Cl₂ was then added dropwise so as to maintain .the internal temperature at −55° C. The mixture was stirred for 5 minutes and then a solution of the above-prepared aminoalcohol (Step D, 0.58 g, 0.7 mmol) in 5 ml anhydrous CH₂Cl₂ was added dropwise. After complete addition, temperature was allowed to raise to −20° C. during minutes. The solution was then again cooled to −55° C. for 0.5 hour. NEt₃ was then added (0.48 ml, 3.5 mmol, 5.0 eq.) so as to maintain internal temperature at −55° C. After 5 minutes a saturated solution of citric acid (2 ml) was added. The mixture was allowed to warm up to room temperature and 40 ml of CH₂Cl₂ was added.

Phases were separated and the organic phase was washed with water and brine, dried over $Na_2SO_4$ and evaporated. The resulting residue was applied to flash chromatography: 50 mg of $Al_2O_3$ (pH: 7.5, pretreated with 3 ml of water; 100 mg eluent: petroleum ether/$CHCl_3$=1:2). The product-containing fractions were pooled and evaporated. The expected compound was obtained as a white foam. Yield: 0.25 g (43%).

Rf: 0.25 (petroleum ether/$CHCl_3$ =1:2)

MS ($C_{38}H_{53}N_6O_9F_5$=832): (CI/$NH_3$): m/e=270 (65%); 257 (100%); 220 (70%).

$^1$H-NMR: ($CDCl_3$, 360 MHz): $\delta$=11.5; 8.4 and 7.9 (broad s, 3H, 3NH); 7.2 (m, 4H, $C_6H_4$); 5.0–4.2 [m, 5H, $NCH_2$-TIC, NCH-TIC, NCH-Pro, (cetone or hydrate)]; 3.8 [broad s, OH of hydrate)]; 3.7–3.0 (3 m, 6H, $CH_2$-TIC, $NCH_2$-Pro, $NCH_2$); 2.4–1.6 (m, 8H, $4CH_{2;1.5}$ (m, 27H, 3 Boc).

$^{19}$F-NMR ($CDCl_3$, $C_6F_6$ ext. ref., 360 MHz) $\delta$=82.81 and 82.65 (2s, 3F, $CF_3CF_2C(OH)_2$; 80.10 and 80.07 (2s, 3F, $CF_3CF_2CO$—); ratio=1:2; 40.58; 40.53 and 40.40 (AB systems badly resolved, 2F, $CF_3CF_2CO$—); 41.05 and 37.92 (AB systems badly resolved, 2F, $CF_3CF_2C(OH)_2$); ratio=2:1.

STEP F

L-Prolinamide, N-[1,-[3-[(aminoiminomethyl)amino]-propyl]-3,3,4,4,4-pentafluoro-2-oxobutyl]-1-D-[(1,2,3,4-tetrahydro-3-isoquinolinyl )carbonyl]-, trichlorohydrate The protected tripeptide analog (Step E, 0.25 g, 0.3 mmol) was dissolved in 25 ml of anhydrous $Et_2O$. A saturated solution of HCl gas in $Et_2O$ (100 ml) was added and the resulting mixture was stirred at room temperature for 48 hours. The mixture was evaporated to dryness. The oily residue was dissolved in a minimum of water and the solution filtered over a Millipore ® filter disk. The filtrate was lyophylized to give the title compound as a white solid. Yield: 0.142 g (89%).

m.p.: 158°–160° C. decomposition, Rf=0.7 (BuOH-/AcOH/$H_2O$=3:1:1).

MS: ($C_{23}H_{29}N_6O_3F_5$=532): (CI/$NH_3$): m/e=533 (MH$^+$, 40%); 274 (45%); 257 (100%); 256 (20%); 220 (30%). Analysis calculated for $C_{23}H_{29}N_6O_3F_5$; 3 HCl; $H_2O$ (659.9) C: 41.86; H: 5.19; N: 12.73 Found: C: 41.41; H: 5.05; N: 12.63. IR: $\upsilon$=3383 CNH; 1654 (C=C; CONH) cm$^{-1}$.

$^1$H-NMR: ($D_2O$, TSP ext. ref., 360 MHz): $\delta$=7.3 (m, 4H, $C_6H_4$); 4.9, 4.8 and 4.7 (3 m, 1H, NCH-TIC); 4.55 and 4.3 [2 m (AB systems badly resolved), 2H, $NCH_2$-TIC); 4.5 superposed (m, 2H, NCH-Pro, NCH); 3.7 (m, 2H, $NCH_2$-Pro); ABX system centered at 3.38 {[A: 3.50 ($J_{HA-HB}$=13 Hz; $J_{HA-HX}$=3 Hz); B: 3.15 ($J_{HB-HA}$=13 Hz; $J_{HA-HX}$=3 Hz)], 2H, $CH_2$-TIC}; 3.25 (broad s, 2H, $NCH_2$); 2.4 and 2.0 (2 m (AB systems badly resolved), 2H, $CH$-$CH_2$-Pro); 2.1 (m, 2H, $CH_2$-Pro); 2.1 and 1.6 (2 m, 4H, $2CH_2$).

$^{19}$F-NMR ($D_2O$, $CF_3COOH$, 360 MHz) $\delta$=−3.62 and −3.65 (2s, 3F, $CF_3$); AB system centered at −47.85 [A: −48.20 ($J_{FA-FB}$=280 Hz); B: −47.49 ($J_{FB-FA}$=280 HZ); AB system centered at −47.97; [A: −48.62 ($J_{FA-FB}$=280 Hz); B: −47.33 ($J_{FB-FA}$280 Hz]; ratio=46:54.

EXAMPLE 5

L-Prolinamide, N-[1-3-[(aminoiminomethyl )amino]-propyl]-3,3,4,4,pentafluoro-2-oxobutyl]-1-[(1,2,3,4-tetrahydro-1-isoquinolinyl)carbonyl]-, dihydrochloride, hydrate

STEP A

N-[(1,1-Dimethylethoxy)carbonyl]-1,2,3,4-tetrahydroisoquinoline-1-carboxylic acid Di-tert-Butyldicarbonate ($Boc_2O$, 8.2 g, 37.6 mmol, 1.1 eq.) was added to a stirred solution of 1,2,3,4-tetrahydroisoquinaldic acid [prepared from isoquinoline-1carboxylic acid according to W. Solomon, J. Chem. Soc., 1947, 129), 6.0 g, 33.8 mmol]and $NEt_3$ (5.2 ml, 37.6 mmol, 1.1 eq.) in 50 ml of tetrahydrofuran and 50 ml of water. The mixture was stirred at room temperature for 16 hours, when tetrahydrofuran was evaporated. The residual aqueous phase was acidified (solid citric acid) and the protected amino acid extracted with AcOEt (three times). The combined organic layers were washed with brine, dried over $MgSO_4$ and evaporated (20 Torr, 30° C. and 0.01 Torr, 20° C.) to afford 8.0 g (85%) of the protected amino acid.

STEP B

N-[(1,1-Dimethylethoxy)carbonyl]-[(1,2,3,4-tetrahydro-1-isoquinolinyl)carbonyl]-L-proline benzyl ester Dicyclohexylcarbodiimide (DCC, 5.38 g, 26 mmol) was added to a stirred and cooled (0° C.) solution of the protected amino acid (Example 5, Step A; 7.2 g, 26 mmol) and hydroxybenzotriazol hydrate (HOBt, 3.98 g, 26 mmol) in 100 ml of dichloromethane and 10 ml of tetrahydrofuran. After stirring for 30 minutes at 0° C., the mixture was allowed to warm up to room temperature for 1 hour and cooled to 0° C. again. L-Proline benzylester hydrochloride (6.3 g, 26 mmol) and N-methylmorpholine (NMM, 3.2 ml, 26 mmol) were added to the mixture and the resulting mixture stirred for 30 minutes at 0° C. and 16 hours at room temperature. Filtration of the mixture and evaporation of the solvents gave an oil which was dissolved in $CH_2Cl_2$. The solution was washed with saturated solutions of citric acid, sodium hydrogen carbonate, and sodium chloride to afford after drying ($MgSO_4$) and evaporation of solvents (20 Tort, 30° C., and 0.01 Torr, 20° C.) 10.5 g of a colorless oil (84%).

Rf=0.8 (AcOEt:petroleum ether=1:2).

STEP C

N-[(1,1-Dimethylethoxy)carbonyl]-[(1,2,3,4-tetrahydro-1-isoquinolinyl)carbonyl]-L-proline A solution of the protected dipeptide (Example 5, Step B; 9.3 g, 20 mmol) and 500 mg of 10% palladium hydroxide on carbon (Pearlman's catalyst) in 150 ml of isopropranol was hydrogenated at room temperature and atmospheric pressure for 14 hours. Filtration from the catalyst and evaporation of the solvent gave 8.0 g of a semisolid oil, which was partially dissolved in methanol/$Et_2O$ (1:1 v/v. Filtration of the mixture gave 2.7 g of a colorless oil. Total yield (93%).

Rf solid=0.80 (BuOH/AcOH/$H_2O$=3/1/1)
Rf oil=0.80 (BuOH/AcOH/$H_2O$=3/1/1)

STEP D

L-Prolinamide, N-[1-3-[[bis[[(1,1-dimethylethoxy)carbonyl]amino]methylene]amino]propyl]-3,3,4,4,4-pentafluoro -2-hydroxybutyl]-N-[(1,1-dimethylethoxy)carbonyl]-1-[(1,2,3,4-tetrahydro-1-isoquinolinyl)-carbonyl]

Dicyclohexylcarbodiimide (DCC, 0.255 g, 1.2 mmol) was added to a cooled (0° C.) and a stirred solution of the above-prepared protected dipeptide (Step D, 0.374 g, 1.2 mmol) and hydroxybenzotriazol hydrate (HOBt, 0.189 g, 1.2 mmol) in 15 ml of dichloromethane. The mixture was stirred for 30 minutes at 0° C. and 1 hour at room temperature and cooled again to 0° C. The Bis-Boc protected arginino analog (see Example 6, Step F; 0.590 g, 1.2 mmol) and N-methylmorpholine (150 ml, 1.4 mmol, 1.1 eq.) were added. The solution was stirred at room temperature for 12 hours. Filtration of the mixture was followed by washing of the filtrate with saturated solutions of citric acid, $KHCO_3$, and brine. The organic solution was dried over $MgSO_4$ and evaporated. The residual oil was applied to flash chromatography on silica gel (10 g, eluent: AcOEt/petroleum ether: ⅔). The tripeptide alcohol analog was isolated as a colorless oil.

Yield: 0.610 g (83%). Rf=0.3 (AcOEt/petroleum ether: 1/1).

STEP E

L-Prolinamide, N-[1,-[3-[[bis[[(1,1-dimethylethoxy)carbonyl-]-amino]methylene]amino]propyl]-3,3,4,4,4-pentafluoro-2-oxobutyl]-N-[(1,1-dimethylethoxy)carbonyl]-1-[(1,2,3,4-tetrahydro-1-isoquinolinyl)-carbonyl]

A solution of oxalylchloride (0.122 ml, 1.4 mmol, 2.0 eq.) in 3 ml of anhydrous $CH_2Cl_2$ was cooled under argon to −60° C. A solution of DMSO (0.197 ml, 2.8 mmol, 4.0 eq.) in 6 ml of anhydrous $CH_2Cl_2$ was then added dropwise to maintain temperature of the solution at −550° C. The mixture was stirred for 5 minutes and a solution of the alcohol prepared in Step D (0.58 g, 0.7 mmol in 5 g of anhydrous $CH_2Cl_2$ was added dropwise. After complete addition, internal temperature was allowed to raise to −20° C. (5 minutes) and the solution was cooled to −55° C. for 1 hour. Triethylamine (0.48 ml, 3.5 mmol) was then added at a rate to maintain internal temperature at −55° C. After 5 minutes, a saturated solution of citric acid (2 ml) was added. The mixture was allowed to warm up to room temperature and 40 ml of $CH_2Cl_2$ was added. Phases were separated and the organic phase was washed with water and brine, dried over $MgSO_4$ and evaporated. The resulting oily residue was flash chromatographed on $Al_2O_3$ (pH: 7.5, pretreated with 3 ml water) 100 g eluent: petroleum ether/$CHCl_3$: ⅓). The product-containing fractions were pooled and evaporated to afford a colorless foam. Yield: 0.30 g (50%).

Rf=0.25 (petroleum ether/$CHCl_3$: ½).

STEP F

L-Prolinamide, N-[1-[3-[(aminoiminomethyl)amino]propyl]-3,3,4,4,4-pentafluoro-2-oxobutyl]-1-[(1,2,3,4-tetrahydro-1isoquinolinyl)carbonyl]-, dihydrochloride, hydrate The protected tripeptide alcohol of Step F (0.30 g, 0.36 mmol) was dissolved in 25 ml of anhydrous $Et_2O$. A saturated solution of HCl gas in $Et_2O$ (100 ml) was added and the resulting mixture was stirred at room temperature for 24 hours. The mixture was filtered and the solid residue further dried (0.01 Torr, 20° C., 16 hours) to give the title ketone (hydrate form) as a white solid. Yield: 0.160 g, (89%).

Rf=0.7 (BuOH/$H_2O$/AcOH: 3/1/1).

EXAMPLE 6

L-Prolinamide, N-methyl-D-phenylalanyl-N-[1-[3-[(aminoiminomethyl)amino]propyl]-3,3,4,4,4-pentafluoro-2-oxobutyl]-, dihydrochloride, hydrate

STEP A

N,N'-[1(Pentafluoropropionyl)-1,4-butanediyl]-bis(benzamide), hydrate

Pentafluoropropionic anhydride (31.8 ml, 50 g, 161 mmol) was added under an atmosphere of $N_2$ to a well stirred powder of the ornithine 5(4H)-oxazolone (see Example 1, Step 2; Reaction Scheme A, Structure (2); 14.05 g, 4.3 mmol). The resulting mixture was stirred at 40° C. for 16 hours. At this time an aliquot (about 50 mg) was taken for a $^1$H- and $^{19}$F-NMR spectrum ($CDCl_3$). The disappearance of the $^1$H-signal at 4.5 ppm indicates disappearance of oxazolone, whereas the $^{19}$F-signals at 42.7; 46.7 (2s, 2×$CF_2$) and 80.0; 80.5 (2s, 2×$CF_3$) indicate the formation of 3'-N-4-bispentafluoropropionyl oxazolone. The additional $^{19}$F-signals were assigned to the excess of pentafluoropropionic anhydride (PFPAA) and the pentafluoropropionic acid (PFPA) formed. Solvents were then evaporated at 55°-60° C. (0.5–1 Torr, dry ice-acetone trap) for about 6 hours to give a thick orange oil. A $^{19}$F-NMR spectrum of another aliquot indicates disappearance of all PFPAA and PFPA. At this time 40 ml of a saturated solution of oxalic acid (15.0 g, 150 mmol) in tetrahydrofuran was added and the resulting orange oil was stirred at 55° C. for 6 hours when effervescence totally stopped. The solvent was evaporated (20 Torr, 30° C.) and the oily residue dissolved in AcOEt. This solution was stirred for 15 minutes at room temperature with a saturated solution of $KHCO_3$ (intended hydrolysis of pentafluoropropionamide). Phases were separated and the organic layer was washed with water, 1N HCl, and brine, dried over $MgSO_4$ and evaporated (20 Torr, 30° C.; then 0.1 Torr, 30° C.). The resulting orange oil (21.7 g) was subjected to flash chromatography on silica gel (500 g; eluent AcOEt/petroleum ether: ⅓) in two batches of about 11 g. Fractions 11–20, containing the N-pentafluoropropionamide A-2 were evaporated to give 7.0 g (27%). Fractions 28–105 containing the ketone A-1 were evaporated to afford 10.1 g (52%) as a white solid.

Total yield: 79% based on oxazolone.

A-1 $^1$H-NMR ($CDCl_3$) δ=8.0–7.85 (m, 5H, aryl, NH), 7.8–7.4 (m, 6H, aryl), 5.5–5.3 (m, 1H, CHCO), 3.9 (broad, t, 2H, $NCH_2$), 2.3–1.8 (m,4H, $2CH_2$).

$^{19}$F-NMR ($CDCl_3$) δ=40.33 (d, J=7.5 Hz, $CF_2CO$), 46.67 (s, $CF_2CONH$), 80.0 (s, $2CF_3$).

A-2 $^1$H-NMR ($CDCl_3$) δ=8.1–7.8 (m, 4H, aryl), 7.7–7.4 (m, 7H, aryl,NH), 6.6 (m, 1H, NH), 5.3 (m, 1H, CHCO), 3.7 (broad t, 2H, $NCH_2$), 2.4–1.8 (m, 4H, $2CH_2$).

$^{19}$F-NMR ($CDCl_3/C_6F_6$) δ=40.3 (d, J=7.5 Hz, $CF_2$), 80.0 (s, $CF_3$).

MS (CI/$NH_3$): 443 (MH+).

A small sample of A-2 (100 mg) was allowed to crystallize from AcOEt/petroleum ether to give 80 mg of analytically pure title compound:

Analysis calculated for $C_{21}H_{19}O_3N_2F_5$ (442.39): C: 57.02; H: 4.33; N: 6.33 Found: C: 57.14; H: 4.23; N: 6.36.

STEP B

N,N'-[1-(2,2,3,3,3-Pentafluoro-1-hydroxypropyl)-1,4-butanediyl]-bis(benzamide)

The reduction of the two ketones A-1 and A-2 was performed in two separate reactions:

1) Reduction of A-1:

$NaBH_4$ (0.43 g, 11 mmol) was added in one portion to a cooled (0° C.) and stirred solution of the pentafluoro-ethyl ketone A-1 (10.1 g, 17.1 mmol) in EtOH (130 ml). The mixture was allowed to warm up to room temperature and further stirred for one hour. Hydrochloric acid (6N) was added carefully until effervescence has stopped. The solution was neutralized with $Na_2CO_3$ and EtOH evaporated. The resulting mixture was redissolved in AcOEt/water and phases separated. The aqueous layer was extracted twice with AcOEt and the combined organic phases washed with water and brine. Drying over $MgSO_4$ and evaporation of solvents afford a white solid, which was subjected to flash chromatography on silica gel (300 g, eluent AcOEt/petroleum ether: 1/1, then 4/1). Product-containing fractions were evaporated to give 5.88 g (77%) of the desired alcohol as a white solid. Rf=0.45-0.50 (AcOEt/petroleum ether: 1/1), two badly separated spots for the diastereoisomers.

Reduction of A-2

As described above for A-1: 6.91 g (15.6 mmol) of the ketone A-2, 300 mg (7.9 mmol) $NaBH_4$, and 90 ml of EtOH afforded 6.05 g (89%) of the alcohol N,N'-[1-(2,2,3,3,3-pentafluoro-1-hydroxypropyl)-1,4-butanediyl]-bis(benzamide) as a white solid, which was in all aspects comparable to the compound obtained above.

$^1$H-NMR ($CDCl_3$,$CD_3OD$) $\delta = 7.8-7.5$ (m, 4H, aryl), 7.45-7.1 (m, 6H, aryl), 4.5 and 4.2 (2 m, 1H, CHOH, ratio 3:1), 3.5 (m, 4H, $2CH_2$).

$^{19}$F-NMR ($CDCl_3$, $CD_3OD$, $C_6F_6$) $\delta$=ABX system centered at 36.3; A: 40.3 ($J_{FA-FB}=280$ Hz, $J_{FA-HX}=3$ Hz); B: 32.3 ($J_{FB-FA}=280$ Hz, $J_{FB-HX}=30$ Hz, $CF_2$), 79.0 (s, $CF_3$)=diastereoisomer 1.

ABX system centered at 35.3; A: 36.3, B: 33.3 (with equal coupling constants as mentioned above)=diastereoisomer 2; ratio 3/1.

Analysis calculated for $C_{21}H_{21}O_3N_2F_5$; (444.40) C: 56.76; H: 4.76; N: 6.30 Found: C: 56.94; H: 4.83; N: 6.29.

STEP C 4,7-Diamino,1,1,1,2,2-pentafluoro-3-heptanol, dihydrochloride

A stirred solution of the above-prepared alcohol (Step B) (11.78 g, 26.6 mmol) in concentrated aqueous hydrochloric acid (240 ml) was heated under stirring to reflux while the progress of hydrolysis was followed by TLC (BuOH/water/AcOH=4/1/1). After 16 hours of reaction time solvent was evaporated and the oily residue subjected a second time to the above conditions. When the complete formation of the bisamino alcohol was indicated by TLC, the solution was cooled to room temperature and solvents evaporated. The oily residue was dissolved in water and the solution washed with $Et_2O$ (3×100 ml). The aqueous layer was evaporated to dryness to afford 8.14 g (99%) of the desired diamino alcohol as a brownish foam.

$^1$H NMR: ($D_2O$) $\delta$=4.6 (m, 1H, $CHOHCF_2$), 3.1 (m, 2H, $NCH_2$), 3.6 (m, 1H, CHN), 2.0 (m, 4H, $2CH_2$).

STEP D

4-Trifluoroacetylamino-7-amino-1,1,1,2,2-pentafluoro-3heptanol, hydrochloride

Trifluoroacetic anhydride (3.55 ml, 25 mmol) was added dropwise to a stirred solution of the diamino alcohol of Step C (3.09 g, 10 mmol) in 50 ml trifluoroacetic acid. After two hours of stirring at room temperature, another 2.5 ml of TFAA was added to the solution and stirring was continued for 10 hours. The solution was evaporated to dryness, giving a brown oil. Trituration with $Et_2O$/petroleum ether afforded a brownish solid, which was filtered and washed with petroleum ether. Drying gave a slightly colored solid of the title compound (3.48 g, 95%), which was pure enough for the following reaction.

$^1$H-NMR ($D_2O$) $\delta$=4.6 (m, 2H, 2CH), 3.1 (m, 2H, $NCH_2$), 2.0-1.7 (m, 4H, $2CH_2$).

$^{19}$F-NMR ($D_2O$, ref. $CF_3CO_2H$) $\delta$=ABX system centered at −49.00) A: −44.00 ($J_{FA-FB}=280$ Hz); B: −54.00 ($J_{FB-FA}=280$ Hz) $J_{FB-HX}=30$ Hz)=isomer 1; ABX centered at −49.33, A: 45.00, B: 40.67 (coupling constants as above)=isomer 2; ratio 4:1. MS: ($CI/NH_3$): 333 (MH+).

STEP E

N-[1-[7-bis[(1,1-Dimethylethoxy)carbonyl]-amino]methylene]amino]-N(4-trifluoroacetylamino)-3-hydroxy-1,1,1,2,2-pentafluoroheptane Bis-Boc-S-methylisothiourea (7,3 g, 25 mmol) was added under an atmosphere of $N_2$ to a well stirred solution of the hydrochloride salt of Step D (5.1 g, 10 mmol) and $NEt_3$(3.5 ml, 25 mmol) in anhydrous tetrahydrofuran (100 ml). The mixture was stirred at 40° C. for 60 hours. Solvents were evaporated (a trap filled with an aqueous solution of $KMnO_4/Na_2CO_3$ was placed between the flask and the pump to avoid poisoning with methanethiol), and the oily residue dissolved in AcOEt. This solution was washed with water, saturated solutions of citric acid, $NaHCO_3$, and brine. Drying over $MgSO_4$ and evaporation of the solvents afforded an oil (10 g) which was subjected to flash chromatography on silica gel (50 g, eluent AcOEt/petroleum ether: ⅛, then 3/1). Product-containing fractions were evaporated to afford 2.92 g (51%) of the protected ω-guanidino-γ-amino alcohol as a colorless foam.

$^1$H-NMR ($CDCl_3$, 360 MHz) $\delta$=11.20 (s, 1H, NH), 10.31 (d, J=10 Hz, 1H, $NHCOCF_3$), 9.73 (broad s, 1H, $NHCH_2$), 4.45 (t, J=9.5 Hz, 1H, CHN), 4.25 d, J=(22 Hz, CHOH), 3.75 (m, 1H, OH ), 3.65 and 3.23 (2 m, 2H, $NCH_2$), 2.1 and 1.9 (2 m, 4H, $2CH_2$), 1.45 and 1.40 (2s, 18H, 2 tert-Boc).

$^{19}$F-NMR ($CDCl_3$, ref. $C_6F_6$) $\delta$=ABX system centered at 35.50; A: 39.33 ($J_{FA-FB}=277$ Hz), B: 32.30 ($J_{FB-FA}=277$ Hz; $J_{FB-HX}=22$ Hz)=isomer 1; ABX system centered at 34.00; A: 40.05 ($J_{FA-FB}277$ Hz), B: 27.5 ($J_{FB-FA}=277$ Hz, $J_{FB-HX}=22$ Hz)=isomer 2, ratio 4:1; 78.87 and 79.40 (2s, ratio 4:1, $CF_3$); 86.12 and 86.53 (2s, ratio 1:4, $CF_3CO$). Analysis calculated for $C_{20}H_{30}F_8N_4O_6$·0.5 $H_2O$ (574.47): C: 41.17; H: 5.36; N: 9.60. Found: C: 41.06; H: 5.15; N: 9.57.

STEP F

N-[1-[7-[bis (1,1-Dimethylethoxy)carbonyl]amino]methylene]amino-4-amino-3-hydroxy-1,1,1,2,2-pentafluoroheptane A freshly prepared aqueous solution of LiOH (1N, 7 ml) was added to a stirred solution of the trifluoroacetamide of Step E (3.0 g, 5.2 mmol) in tetrahydrofuran/water (9/1, 50 ml). The solution was stirred at room temperature for 20 hours, when starting material has disappeared (TLC, AcOEt/petroleum ether: 1/5). Tetrahydrofuran was evaporated and the aqueous solution extracted with $Et_2O$ (4×50 ml). The combined extracts were washed with water and brine, and dried over $MgSO_4$. Evaporation of the solvent afforded 2.18 g (88%) of the above-described aminoalcohol as a white solid.

$^1$H-NMR (CDCl$_3$) δ=11.5 (m, 1H, NH), 8.4 (m, 1H, NH), 4.1 and 3.9 (2 m, 1H, CHOH), 3.5 and 3.2 (2 m, 3H, CHN, NCH$_2$), 2.5 (m, 2H, NH$_2$), 1.9–1.4 (m, 4H, 2CH$_2$), 1.50 (s, 18H, 2 tert-Boc).

$^{19}$F-NMR (CDCl$_3$) δ=ABX system centered at 37.3; A: 43.67, (J$_{FA\text{-}FB}$=280 Hz; J$_{FB\text{-}HX}$=22 Hz, CF$_2$, isomer 1), 79.0 (s, CF$_3$) and ABX system centered at 39.0 (coupling constant as above), (CF$_2$ isomer 2), 79.5 (s, CF$_3$); ratio 4:1. Analysis calculated for C$_{18}$H$_{31}$F$_5$N$_4$O$_5$ (478.46): C: 45.19; H: 6.53; N: 11.71. Found: C: 45.13; H: 6.44; N: 11.56.

STEP G

L-Prolinamide, N-[(1,1-dimethylethoxy)carbonyl]-N-methyl-D-phenylalanyl-N-[1-[3-[[bis[[(1,1-dimethylethoxy)carbonyl]amino]methylene]amino]propyl]-3,3,4,4,4-pentafluoro-2-hydroxybutyl]

Dicyclohexylcarbodiimide (0.96 g, 4.7 mmol) was added to a stirred and cooled (0° C.) solution of Boc-N(methyl)-D-Phe-Pro-OH (1.78 g, 4.7 mmol) and N-hydroxybenzotriazole (0.711 g, 4.7 mmol) in CH$_2$Cl$_2$ (50 ml). The mixture was stirred for 30 minutes at 0° C., when the above-prepared amino alcohol (Step F) (2.22 g, 4.64 mmol) and NMM (0.52 ml, 4.7mmol) were added. The resulting mixture was further stirred for 0.5 hour at 0° C. and then allowed to warm up to room temperature. Stirring was continued for 16 hours at room temperature. Filtration of the precipitated DCU and washing of the filtrate with saturated solutions of citric acid, KHCO$_3$, and brine was followed by drying over MgSO$_4$ and evaporation of the solvent to afford a viscous oil. Flash chromatography on silica gel (150 g, eluent AcOEt/petroleum ether: 1/1) and evaporation of the product-containing fractions afforded 3.09 g (70%) of the desired tripeptide alcohol as a colorless oil.

$^1$H-NMR: (CD$_3$OD, 360 MHz) δ=7.2 (m, 5H, aryl), 5.1–4.9 (2 m, 1H, CH-Phe), 4.4–3.9 (m, 3H, CH-Pro, CHOH, CHN), 3.7–3.3 and 3.2–2.9 (2 m, 6H, 2NCH$_2$, Phe-CH$_2$), 2.85–2.7 (5 s, 3H, NCH$_3$), 2.3–1.6 (m, 8H, 4CH$_2$), 1.5–1.1 (6 s, 27H, 3 tert-Boc).

$^{19}$F-NMR (CD$_3$OD, C$_6$F$_6$ ext. ref., 360 MHz) δ=about 3 ABX systems centered at 43.7 (CF$_2$-isomer 1 and 2; cis-trans-isomers) and 81.80, 81.55, 81.30 (3 s, CF$_3$ of diff. isomers). MS (FAB): 837 (MH+).

STEP H

L-Prolinamide, N-[(1,1-dimethylethoxy)carbonyl]-N-methyl-D-phenylalanyl-N-[1-[3-[[bis[[(1,1-dimethylethoxy)carbonyl]amino]methylene]amino]propyl]-3,3,4,4,4-pentafluoro-2-oxobutyl]

A 100 ml three-necked flask equipped with a magnetic stirring bar, thermometer, and a N$_2$-inlet was charged with a solution of oxalylchloride (0.52 ml, 5.7 mmol) in 5 ml of anhydrous CH$_2$Cl$_2$. After cooling the solution to −60° C., a solution of dimethylsulfoxide (1.2 ml, 14.3 mmol) in 10 ml of anhydrous CH$_2$Cl$_2$ was added via a syringe at a rate to keep internal temperature at −55° C. The mixture was stirred for 15 minutes at −55° C., when the alcohol of Step F (3.0 g, 3.58 mmol) in 20 ml of anhydrous CH$_2$Cl$_2$ was added dropwise. After complete addition, the cooling bath was removed and stirring continued until internal temperature reaches −20° C. At this temperature stirring was continued for about 5 minutes and the solution cooled again to −55° C. At this temperature NEt$_3$ (2.5 ml, 17.9 mmol) was added at a rate to keep internal temperature at −55° C. Finally a saturated citric acid solution (10 ml) was added. The mixture was allowed to warm up to room temperature and 200 ml of CH$_2$Cl$_2$ was added. Phases were separated and the organic layer washed with water, a saturated solution of NaHCO$_3$, and brine. Drying over MgSO$_4$ and evaporation of solvents give a colorless oil (about 3 g) which was subjected to flash chromatography on silica gel (100 g, eluent AcOEt/petroleum ether: 1/3, then 1/1, then 2/1). Product-containing fractions were evaporated to obtain 1.0 g (33%) of the above-described pure pentafluoro ketone as a colorless foam. About 1.6 g of a mixture of the above-described ketone and starting alcohol described in Step G was recovered, which can be recycled for another oxydation.

$^1$H-NMR (CDCl$_3$, 360 MHz) δ=11.5 (m, 1H, NH), 8.5 (m, 1H, NH), 7.8 (m, 1H, NH), 7.2 (m, 5H, aryl), 5.1–4.3 (m, 3H, α-CH-Phe, α-CH-Pro, α-CHCO), 3.7–3.1 and 3.1–2.6 (2 m, 9H, 2NCH$_2$, CH$_2$C$_6$H$_5$, NCH$_3$), 2.2–1.6- (m, 8H, 4CH$_2$), 1.5–1.2 (m, 27H, 9CH$_3$).

$^{19}$F-NMR (CDCl$_3$, 360 MHz) δ=40.33 and 40.19 (2 s, CF$_2$CO), ABX systems centered at 39.0 (CF$_2$), 80.0 (s, CF$_3$), 82.7 and 82.9 (2 s, CF$_3$), ratio 4:1.

STEP I

L-Prolinamide, N-methyl-D-phenylalanyl-N -[1-[3-[(aminoiminomethyl)amino]propyl]-3,3,4,4,4-pentafluoro-2-oxobutyl]-, dihydrochloride, hydrate 0.9 g (1.07 mmol) of the tripeptide derivative of Step H was dissolved in 50 ml on anhydrous Et$_2$O. 200 ml of a saturated HClgas/Et$_2$O solution was added and the resulting solution stirred at room temperature for 48 hours (under exclusion of moisture). Petroleum ether (about 100 ml) was added and the precipitate filtered under N$_2$. Drying of the filter residue (0.1 Tort, 40° C.) afforded 0.6 g of a white amorphous powder which was dissolved in water (20 ml) and the solution filtered over a Millipore ® filter disk. The filtrate was then lyophilized to give 0.5 g (82%) of the title compound as a white fluffy powder.

$^1$H-NMR (D$_2$O) δ=7.55 (m, 3H, aryl), 7.30 (m, 2, aryl), 4.55 (m, 1H, CH-Phe), 4.38 (m, 1H, CH-Pro), 4.27 [m, 1H, CHN—C(OH)$_2$], 3.50 (m, 1H, HCH$_A$-Pro), 3.37 (m, 1H, C$_6$H$_5$CH$_A$), 3.25 (m, 2H, NCH$_2$-guanidine), 3.15 (m, 1H, C$_6$H$_5$CH$_B$), 2.75 (s, broad, 3H, CH$_3$N), 2.73–2.63 (m, 1H, NCH$_B$-Pro), 2.2–1.4 (m, 8H, 4CH$_2$). Impurities of about 9% can be seen at 6.2, 3.7 and 1.2 ppm.

$^{19}$F-NMR (D$_2$O, CF$_3$CO$_2$H ext. ref.) δ=−3.65 and −3.71 (2 s, ratio, 45:55, 3F, CF$_3$), 1 AB system centered at −47.80; A: −47.44 (J$_{FA\text{-}FB}$=281 Hz); B: −48.16 (J$_{FB\text{-}FA}$=281 Hz), AB system centered at −48.09; A: −47.64 (J$_{FA\text{-}FB}$=281 Hz), −48.53 (J$_{FB\text{-}FA}$=281 Hz)=CF$_2$ of the two diastereoisomers, ratio 45:55, impurities of remaining alcohol described in Step G at −6.9 and −54.0 (about 5%) and unknown structure at −3.3 and −45.5 (9%).

EXAMPLE 7

L-Prolinamide, N-methyl-D-phenylalanyl-N-[1-[3,[(aminoiminomethyl)amino]propyl]-3,3-difluoro-2-oxohexyl]-, dihydrochloride, hydrate

STEP A

N-[1-[4-[bis[(1,1-Dimethylethoxy)carbonyl]amino]methylene]amino]-1-nitrobutane

Bis-Boc-S-methylisothiourea (13.8 g, 47.6 mmol) was added at a time to a stirred solution of 4-amino-1-nitrobutane, hydrochloride [prepared according to W.

Keller-Schierlein, P. Mertens, V. Prelog, and A. Walser, *Helv. Chim. Acta,* 48, Fasc. 4 (1965) 710](2.1 g, 13.6 mmol) and 6.6 ml (47.6 mmol) of NEt$_3$ in 40 ml of anhydrous dimethylformamide. The mixture was stirred under an atmosphere of argon for 14 hours. 200 ml of Et$_2$O were added and the solution washed with water and concentrated solutions of citric acid, sodium bicarbonate, and sodium chloride. The organic layer was dried over MgSO$_4$ and evaporated (20 Tort, 30° C.) to afford 15 g of a yellow oil. Flash chromatography on silica gel (0.500 g, eluent: AcOEt/petroleum ether: 1/5) and evaporation of the product-containing fractions (20 Torr, 30° C. and then 0.01 Torr, 20° C.) afforded 3.48 g (71%) of the protected guanidino derivative as a white solid. Rf=0.5 (AcOEt/petroleum ether: ½). m.p.: 94°–96° C.

STEP B

N-1-[9-[bis [(1,1-Dimethylethoxy )carbonyl]amino]methylene]amino-4,4-difluoro-5-hydroxy-6-nitro-1-nonene A mixture of the above-prepared nitroderivative (Step A, 0.48 g, 1.33 mmol) and 2,2-difluoro-pentene-1-al, ethyl hemiacetal (0.283 g, 1.7 mmol) and a catalytic amount of potassium carbonate (about 40 mg) was stirred for 14 hours at 40° C. AcOEt (50 ml) was added and the resulting mixture washed with water and brine. Drying over MgSO$_4$ of the organic layer and evaporation of the solvent (20 Torr, 30° C.) afforded a colorless oil (0.57 g), which was applied to flash chromatography on silica gel (20 g, eluent: AcOEt/petroleum ether: 1/5). The product-containing fractions were pooled and evaporated (20 Torr, 30° C. and 0.01 Torr, 20° C.) to give 0.332 g (52%) of the desired nitroalcohol as a slightly yellow solid.

Rf=0.4 (AcOEt/petroleum ether: ½).

STEP C

N-1-[9-[bis[(1,1-Dimethylethoxy)carbonyl]amino]methylene]amino-4,4-difluoro-5-hydroxy-6-aminononane To a stirred solution of the above-prepared nitroalcohol (Step B, 0.33 g, 0.67 mmol) in i.-propanol (40 ml) was added 0.1 g of freshly prepared Raney-Nickel. The mixture was applied to hydrogenation under atmospheric pressure for 16 hours when H$_2$ consumption had completed. Filtration of the mixture and evaporation of the solvent (20 Torr, 30° C. and 0.01 Torr, 20° C.) afforded the desired difluoroamino alcohol as a colorless oil. Yield: 302 mg (93%).

STEP D

L-Prolinamide, N-[(1,1-dimethylethoxy) carbonyl]-N-methyl-D-phenylalanyl-N-[1-[3[[bis[[(1,1-dimethylethoxy)carbonyl]amino]methylene]amino]propyl]3,3-difluoro -2-hydroxyhexyl]

Following the procedure as described for Example 6, Step G: with 0.23 g (0.61 mmol) of Boc-N-(methyl)-D-Phe-Pro-OH, 0.093 g (0.61 mmol) of HOBt, 0.126 g (0.61 mmol) of DCC, 0.08 g (0.75 mmol) of N-methylmorpholine, and 0.23 g (0.61 mmol) of the above-prepared difluoroamino alcohol (Step C), in 10 ml of CH$_2$Cl$_2$ and flash chromatography of the crude reaction product on silica gel (20 g, eluent: AcOEt/petroleum ether: ½–1/1) 0.24 g (49%) of the protected tripeptide analog were obtained as a colorless oil.

Rf=0.4–0.6 (AcOEt/petroleum ether: 1/1).

STEP E

L-Prolinamide, N-[(1,1-dimethylethoxy)carbonyl]-N-methyl-D-phenylalanyl-N-1-[3-[[bis [[(1,1-dimethylethoxy )carbonyl]amino]methylene]amino]propyl]-3,3-difluoro-2-oxohexane]

The product of Step D (0.24 g, 0.29 mmol) was oxidized to the corresponding ketone following the procedure described in Example 5, Step H with the following quantities: 0.051 ml (0.59 mmol) of oxalyl chloride, 0.084 ml (1.1 mmol) of DMSO, and 0.2 ml (2 mmol) of NEt$_3$ in 6 ml of anhydrous CH$_2$Cl$_2$. Flash chromatography of the crude reaction product (0.19 g) on silica gel (10 g, eluent AcOEt/petroleum ether: ⅜) and evaporation of the product-containing fractions afforded 0.16 g (67%) of the desired ketone as a colorless oil.

Rf=0.2–0.3 (two spots) (AcOEt/petroleum ether: ⅜).

STEP F

L-Prolinamide, N-methyl-D-phenylalanyl-N-[1-[3-[(aminoiminomethyl)amino]propyl]-3,3-difluoro-2-oxohexyl]-dihydrochloride, hydrate To 0.15 g (0.186 mmol) of the above-prepared ketone (Step E) was added 50 ml of a saturated HCl gas/Et$_2$O solution and the mixture was stirred for 48 hours. The solvent was evaporated and the solid residue dissolved in water. Filtration of the solution on a Millipore ® filter disk and lyophilization of the filtrate afforded 0.11 g (100%) of the title compound as a yellow solid.

Rf=0.4 and 0.45 (two diastereoisomers) (BuOH-/AcOH/H$_2$O: 3/1/1).

AS stated above, the compounds of this invention (IA and IB) possess the property of exhibiting significant inhibition of thrombin indicating that they are effective anti-coagulants useful for the prevention of both venous and arterial thrombotic diseases.

Using standard in vitro assay methodology for determining inhibitory activity of thrombin as well as anticoagulant activities in human plasma using activated thromboplastin times (aPTT) and thrombin times (TT), it is to be found that the compounds of Formulae IA and IB are effective anticoagulants.

| ANTICOAGULANT EFFECT IN HUMAN PLASMA | | |
|---|---|---|
| | ID$_2$[a] (μM) | |
| Compound | $_a$PTT[b] | TT[b] |
| D-CH$_3$Phe—Pro—Arg—CF$_3$ | 218 | 108 |
| D-Phe—Pro—Arg—CF$_3$ | 148 | 43 |
| D-Phe—Pro—Arg—CF$_2$CF$_3$ | 2 | 1 |

[a]Amount required for doubling the clotting time;
[b]$_a$PTT, activated partial thromboplastin time;
TT, thrombin time.

In vivo anti-thrombotic effects in rats may also be utilized for evaluation. For example, in the FeCl$_3$—induced thrombosis model wherein D-Phe-Pro-Arg-CF$_2$CF$_3$ was administered intravenously as a 10 mg/kg of body weight injection, followed by a continuous 1 mg/kg/minute infusion, the compound was capable of preventing occlusion in two rats and prolonging occlusion in the other 2 of the 4 rats. Thus, based upon standard in vitro and i vivo assay methodology it is to be found that the compounds of this invention, at doses within the range of about 2 to 50 mg per kilogram of body weight (with 2 to 20 for preferred compounds) per day will be useful in the treatment of thrombophlebitis and coronary thrombosis, as well as other venous and arterial thrombotic disease states. Of course, actual dosage and frequency will vary dependent upon the nature and severity of the condition, age, general health conditions and such other factors well known and appreciated by the skilled attending diagnostician.

In addition to the foregoing use of the novel compounds of Formulae IA and IB as inhibitors of thrombin, another aspect of this invention is the use of these compounds as effective inhibitors of human lung tryptase and, as such, are useful in the treatment of asthma.

Using standard in vitro methodology for determining inhibitory activity of tryptase (Journal of Biological Chemistry, Vol. 261, June 5, pp. 7372–7379, 1986), the following results have been obtained:

| HUMAN LUNG TRYPTASE | | | |
|---|---|---|---|
| Rate Constants[a] | $k_{on}$, $M^{-1}s^{-1}$ | $k_{off}$, $s^{-1}$ | $K_i$, M |
| D-Phe—Pro—Arg—CF$_3$ | 290 ± 20 | $1.5 \times 10^{-4} \pm 1.5 \times 10^{-5}$ | $5.0 \times 10^{-7}$ |
| D-CH$_3$—Phe—Pro—Arg—CF$_3$ | 200 ± 10 | $1.5 \times 10^{-5} \pm 2.4 \times 10^{-6}$ | $8.0 \times 10^{-8}$ |
| D-Phe—Pro—Arg—CF$_2$CF$_3$ | 1200 ± 40 | $6.8 \times 10^{-4} \pm 3.6 \times 10^{-5}$ | $6.0 \times 10^{-7}$ |
| D-3-TIC—Pro—Arg—CF$_2$CF$_3$ | 4700 ± 200 | $3.4 \times 10^{-4} \pm 8.3 \times 10^{-5}$ | $7.5 \times 10^{-8}$ |

[a]Rate constants were determined by progress curve analysis using a non-linear regression program (ENZFITTER)

Based upon the foregoing type assay, as well as by comparison with other compounds also known to possess tryptase inhibitory activity, it is to be found that the compounds of this invention, in their end-use application for the treatment of asthma will be about 1–100 mg per treatment; the dose regimen, of course, being dependent on the severity of the attack, the age and general condition of the patient, as well as other factors well appreciated by the attending diagnostician.

Although it may be possible that some of the administered tripeptides of this invention may survive passage through the gut following oral administration, it is preferred that the compounds be utilized via a non-oral administration. Subcutaneous, intravenous, intramuscular or intraperitoneal administrations, depot injections, implant preparations and such other non-oral methods are the preferred manners by which the compounds may be utilized. In those instances wherein asthma is being treated it is preferred to utilize metered dose aerosols or by application to the mucous membranes, (e.g. nose, throat and bronchial tubes) in an aerosol can containing a peptide derivative of this invention in the form of a spray or dry powder pharmaceutical formulation.

For a parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by Dow-Corning Corporation.

The compounds of this invention can also be administered topically. This can be accomplished by simply preparing a solution of the compound to be administered, preferably using a solvent known to promote transdermal absorption such as ethanol or dimethyl sulfoxide (DMSO) with or without other excipients. Preferably topical administration will be accomplished using a patch either of the reservoir and porous membrane type or of a solid matrix variety.

Some suitable transdermal devices are described in U.S. Pat. Nos. 3,742,951, 3,797,494, 3,996,934, and 4,031,894. These devices generally contain a backing member which defines one of its face surfaces, an active agent permeable adhesive layer defining the other face surface and at least one reservoir containing the active agent interposed between the face surfaces. Alternatively, the active agent may be contained in a plurality of microcapsules distributed throughout the permeable adhesive layer. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

In another device for transdermally administering the compounds in accordance with the present invention, the pharmaceutically active compound is contained in a matrix from which it is delivered in the desired gradual, constant and controlled rate. The matrix is permeable to the release of the compound through diffusion or microporous flow. The release is rate controlling. Such a system, which requires no membrane is described in U.S. Pat. No. 3,921,636. At least two types of release are possible in these systems. Release by diffusion occurs when the matrix is non-porous. The pharmaceutically effective compound dissolves in and diffuses through the matrix itself. Release by microporous flow occurs when the pharmaceutically effective compound is transported through a liquid phase in the pores of the matrix.

The preferred compounds of this invention (IA and IB) which are of particular interest are those compounds specified in the following charts

| Compounds of Formula IA | | | | | |
|---|---|---|---|---|---|
| R$_1$ | R$_2$ | P$_3$ | P$_2$ | P$_1$ | R$_3$ |
| H | CH$_3$ | D-Phe | L-Pro | Arg | CF$_3$ |
| H | CH$_3$ | D-Phe | L-Pro | Arg | C$_2$F$_5$ |
| CH$_3$ | CH$_3$ | D-Phe | L-Pro | Arg | CF$_3$ |
| CH$_3$ | CH$_3$ | D-Phe | L-Pro | Arg | C$_2$F$_5$ |
| H | CH$_3$ | D-Phe | L-Pro | Arg | CF$_2$(CH$_2$)$_2$CH$_3$ |
| H | H | D-Phe | L-Pro | Arg | CF$_2$(CH$_2$)$_2$CH$_3$ |
| H | CH$_3$ | D-CHM | L-Pro | Arg | C$_2$F$_5$ |
| H | CH$_3$ | D-Phe | L-Pro | Arg | CF$_2$(CH$_2$)$_2$CO$_2$Et |
| H | CH$_3$ | D-Phe | L-Pro | Arg | CF$_2$(CH$_2$)$_2$CONHCH$_3$ |
| H | CH$_3$ | D-Phe | L-Pro | Arg | CF$_2$(CH$_2$)$_4$CONHCH$_3$ |
| H | CH$_3$ | D-CH | L-Pro | Arg | C$_2$F$_5$ |

-continued

Compounds of Formula IA

| R₁ | R₂ | P₃ | P₂ | P₁ | R₃ |
|---|---|---|---|---|---|
| CH₃ | CH₃ | D-CH | L-Pro | Arg | C₂F₅ |
| CH₃ | CH₃ | D-CHM | L-Pro | Arg | C₂F₅ |
| CH₃ | CH₃ | D-CHM | L-Pro | Arg | CF₂(CH₂)₂CO₂Et |
| CH₃ | CH₃ | D-CH | L-Pro | Arg | CF₂(CH₂)₂CO₂Et |
| H | CH₃ | D-CHM | L-Pro | Arg | CF₂(CH₂)₂CH₃ |
| H | CH₃ | D-CHM | L-Pro | Arg | CF₂(CH₂)₂CO₂Et |
| H | CH₃ | D-CH | L-Pro | Arg | CF₂(CH₂)₂CH₃ | wherein CH is cyclohexyl, CHM is cyclohexylmethyl, both being the substituents on the o-carbon atom of the modified $P_3$-α-amino acid of the depicted tripeptide of Formula IA, and Et is ethyl.

Compounds of Formula IB

| P₃ | P₂ | P₁ | R₃ |
|---|---|---|---|
| 2a | L-Pro | Arg | C₂F₅ |
| 2b | L-Pro | Arg | C₂F₅ |
| 2c | L-Pro | Arg | C₂F₅ |
| 2'a | L-Pro | Arg | C₂F₅ |
| 2'b | L-Pro | Arg | C₂F₅ |
| 2'c | L-Pro | Arg | C₂F₅ |
| 2'b | L-Pro | Arg | CF₂(CH₂)₂CH₃ |
| 2'c | L-Pro | Arg | CF₂(CH₂)₂CH₃ |
| 2b | L-Pro | Arg | CF₂(CH₂)₂CH₃ |
| 2c | L-Pro | Arg | CF₂(CH₂)₂CH₃ |
| 2b | L-Pro | Arg | CF₂(CH₂)₂CO₂Et |
| 2'b | L-Pro | Arg | CF₂(CH₂)₂CO₂Et |
| 2b | L-Pro | Arg | CF₂(CH₂)₄CO₂Et |
| 2'b | L-Pro | Arg | CF₂(CH₂)₄CO₂Et |
| 2b | L-Pro | Arg | CF₂(CH₂)₃CH₃ |
| 2'b | L-Pro | Arg | CF₂(CH₂)₂CH₃ |
| 2b | L-Pro | Arg | CF₂(CH₂)₂CONHCH₃ |
| 2'b | L-Pro | Arg | CF₂(CH₂)₂CONHC₂H₅ |
| 2b | L-Pro | Arg | CF₂(CH₂)₃CO₂Et |
| 2'b | L-Pro | Arg | CF₂(CH₂)₃CONHCH₃ | wherein the $P_3$ moieties 2a, b and c, and 2'a, b and c are as previously defined, which, when combined with the carbonyl moiety to which they are attached, form the modified $P_3$-α-amino acid of the depicted tripeptides of Formula IB.

What is claimed is:

1. A compound of formulae their isomers or mixtures thereof, the hydrates or the pharmaceutically acceptable salts thereof, with the proviso that when $R_1$ and $R_2$ are both H or when A is phenyl, then $R_3$ is other than —$CF_3$ or —$CF_2CF_3$, wherein m is zero, one or two, n is zero or one, with the proviso that the sum of m and n is less than three and greater than zero, q is zero or one with the proviso that the sum of both q's is zero or 2, $R_1$ is H or $C_{1-7}$ alkyl, $R_2$ is H or $C_{1-7}$ alkyl, or $R_1$ and $R_2$ taken together with the nitrogen atom to which they are attached form pyrrolidinyl or piperidinyl, $R_3$ is —$CF_3$, —$CF_2CF_3$, —$CF_2(CH_2)_tCH_3$, —$CF_2(CH_2)_tCOOR$—$CF_2(CH_2)_tCONHR_4$, —$CF_2(CH_2)_tCH_2OR_4$ or —$CF_2(CH_2)_vCH=CH_2$, with t being 2, 3 or 4, and v is 1, 2 or 3, $R_4$ is H or $C_{1-6}$ alkyl, A is phenyl or cyclohexyl, B is $(CH)_4$ or $(CH_2)_4$ which, when taken together with the two carbon atoms to which it is attached, forms a phenyl or cyclohexyl moiety.

2. A compound of claim 1 wherein the $R_3$ moiety is selected from the group consisting of —$CF_3$, —$CF_2CF_3$, —$CF_2(CH_2)_2CH_3$, —$CF_2(CH_2)_2CO_2Et$, —$CF_2(CH_2)_2CONHCH_3$ and —$CF_2(CH_2)_4CONHCH_3$.

3. A compound of claim 2 having the structure of Formula IA wherein A is phenyl, n is one, $R_1$ is H and $R_2$ is $C_{1-7}$ alkyl and the $R_3$ moiety is selected from the group consisting of —$CF_2(CH_2)_2CH_3$, —$CF_2(CH_2)_2CO_2Et$, —$CF_2(CH_2)_2CONHCH_3$ and —$CF_2(CH_2)_4CONHCH_3$.

4. A compound of claim 3 wherein $R_2$ is methyl.

5. A compound of claim 2 having the structure of Formula IA wherein A is cyclohexyl, $R_1$ is H and $R_2$ is $C_{1-7}$ alkyl.

6. A compound of claim 5 wherein $R_2$ is methyl and n is one.

7. A compound of claim 2 having the structure of Formula IB wherein the $R_3$ moiety is selected from the group consisting of —$CF_3$, —$CF_2CF_3$, —$CF_2(CH_2)_2CH_3$, —$CF_2(CH_2)_2CO_2Et$, —$CF_2(CH_2)_2CONHCH_3$ and —$CF_2(CH_2)_4CONHCH_3$.

8. A compound of claim 7 wherein B is $(CH)_4$, each q is zero, m is two, and n is zero.

9. A compound of claim 7 wherein B is $(CH)_4$, each q is zero, m is one, and n is one.

10. A compound of claim 4 wherein $R_3$ is —$CF_2(CH_2)_2CH_3$.

11. A compound of claim 8 wherein $R_3$ is —$CF_2(CH_2)_2CH_3$.

12. A compound of claim 9 wherein $R_3$ is —$CF_2(CH_2)_2CH_3$.

* * * * *